United States Patent
Park et al.

(10) Patent No.: US 10,439,155 B2
(45) Date of Patent: Oct. 8, 2019

(54) QUANTUM DOT LIGHT-EMITTING DIODE AND QUANTUM DOT LIGHT-EMITTING DEVICE HAVING THE SAME

(71) Applicant: LG Display Co., Ltd., Seoul (KR)

(72) Inventors: Jae-Hyun Park, Paju-si (KR); Kyu-Nam Kim, Paju-si (KR); Young-Ju Ryu, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 16/129,123

(22) Filed: Sep. 12, 2018

(65) Prior Publication Data

US 2019/0081263 A1 Mar. 14, 2019

(30) Foreign Application Priority Data

Sep. 12, 2017 (KR) ........................ 10-2017-0116451

(51) Int. Cl.
| | |
|---|---|
| *H01L 51/50* | (2006.01) |
| *H01L 51/52* | (2006.01) |
| *G01N 33/58* | (2006.01) |
| *H01L 51/42* | (2006.01) |
| *H01L 33/06* | (2010.01) |

(Continued)

(52) U.S. Cl.
CPC ......... *H01L 51/502* (2013.01); *G01N 33/588* (2013.01); *G02B 6/0229* (2013.01); *H01L 21/02601* (2013.01); *H01L 25/167* (2013.01); *H01L 31/035218* (2013.01); *H01L 33/06* (2013.01); *H01L 51/426* (2013.01); *H01L 51/5056* (2013.01); *H01L 51/5072* (2013.01); *H01L 51/5092* (2013.01); *H01L 51/5218* (2013.01); *H01L 51/5221* (2013.01); *B82Y 20/00* (2013.01); *H01L 27/124* (2013.01)

(58) Field of Classification Search
CPC ....... H01L 21/02601; H01L 31/035218; H01L 33/06; H01L 51/426; H01L 25/167; G01N 33/588; G02B 6/0229
See application file for complete search history.

(56) References Cited

U.S. PATENT DOCUMENTS

| | | | |
|---|---|---|---|
| 2010/0117029 A1* | 5/2010 | Ying | B82Y 15/00 |
| | | | 252/301.36 |
| 2011/0129420 A1* | 6/2011 | Allen | A61K 49/0067 |
| | | | 424/9.1 |

(Continued)

FOREIGN PATENT DOCUMENTS

| | | |
|---|---|---|
| JP | 2010-114079 A | 5/2010 |
| JP | 2017-516320 A | 6/2017 |

(Continued)

OTHER PUBLICATIONS

Lim et al., "InP@ZnSeS, Core@Composition Gradient Shell Quantum Dots with Enhanced Stability," *Chem. Mater.* 23:4459-4463, 2011.

(Continued)

*Primary Examiner* — Ngan V Ngo
(74) *Attorney, Agent, or Firm* — Seed IP Law Group LLP

(57) ABSTRACT

The present disclosure is directed to quantum dots comprising a core-shell structure and a novel arrangement of ligands thereon. Light emitting diodes including the quantum dots, light emitting devices including the same as well as methods associated with preparation and use of such compounds and devices are also provided.

17 Claims, 11 Drawing Sheets

(51) Int. Cl.
  *G02B 6/02* (2006.01)
  *H01L 31/0352* (2006.01)
  *H01L 25/16* (2006.01)
  *H01L 21/02* (2006.01)
  *B82Y 20/00* (2011.01)
  *H01L 27/12* (2006.01)

(56) References Cited

U.S. PATENT DOCUMENTS

2015/0053914 A1* 2/2015 Kurtin ............... H01L 33/502 257/13
2015/0183939 A1* 7/2015 Lequeux ............ A61K 49/0067 436/501
2016/0032183 A1* 2/2016 Ghosh ................ C09K 11/025 438/47
2017/0005226 A1* 1/2017 Mangum ............. C09K 11/025
2017/0029697 A1* 2/2017 Ghosh ................. C09K 11/883
2018/0033988 A1* 2/2018 Walter .................... H01L 33/06
2018/0354244 A1* 12/2018 Jen-La Plante ........ C09K 11/02
2019/0077954 A1* 3/2019 Tangirala ............. C08K 5/5313

FOREIGN PATENT DOCUMENTS

KR 10-1478448 B1 12/2014
WO 2017/038487 A1 3/2017

OTHER PUBLICATIONS

Zhang et al., "Fluorescence Anisotropy as a Reliable Discrimination of Ligand-Asymmetric and Symmetric Mn-Doped ZnS Quantum Dots," *Anal. Chem.* 88(19): (Abstract), 2016.

* cited by examiner

FIG. 4
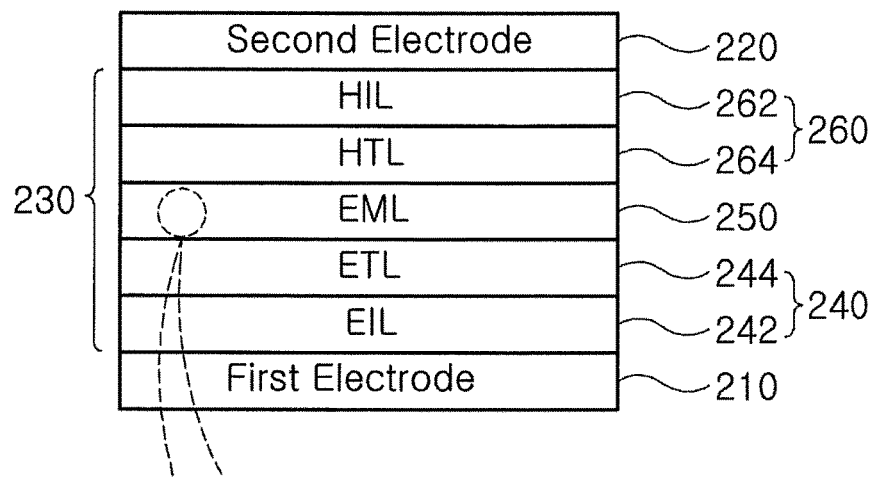
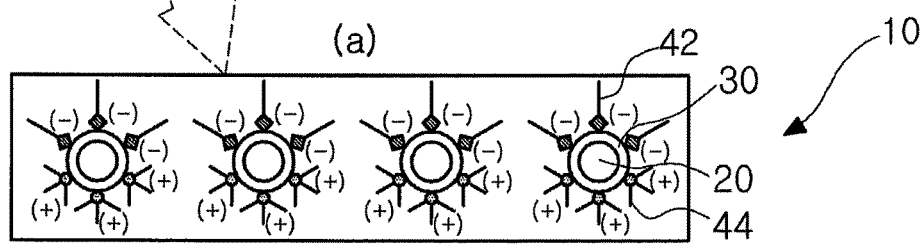
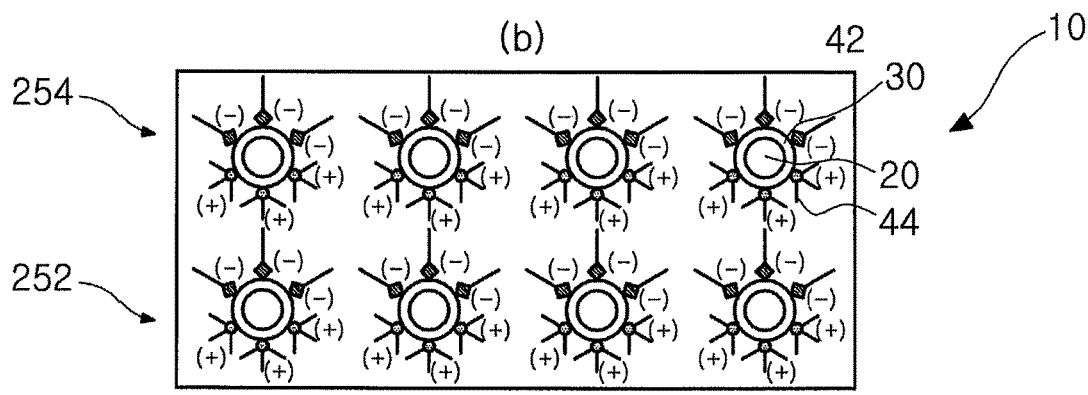

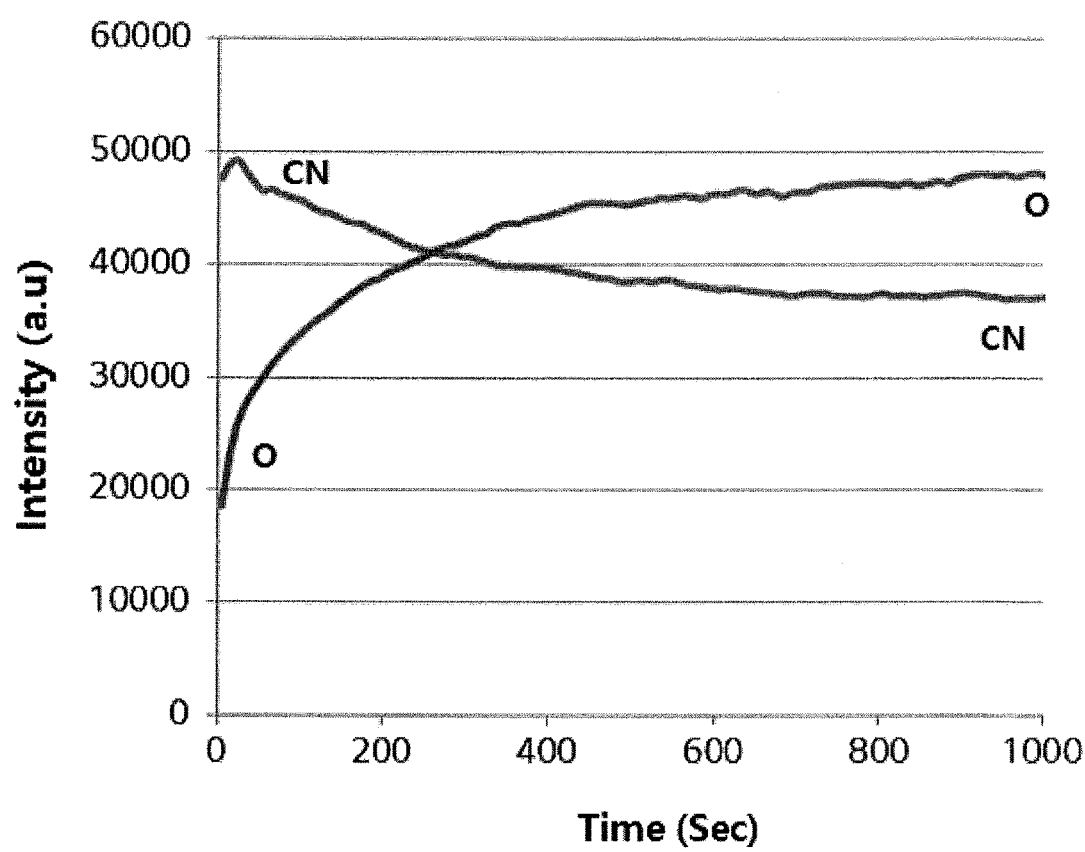

QUANTUM DOT LIGHT-EMITTING DIODE AND QUANTUM DOT LIGHT-EMITTING DEVICE HAVING THE SAME

CROSS-REFERENCE TO RELATED APPLICATIONS

This application claims the benefit under 35 U.S.C. § 119(a) of Korean Patent Application No. 10-2017-0116451, filed in Korea on Sep. 12, 2017, which is incorporated herein by reference in its entirety.

BACKGROUND

Technical Field

The present disclosure relates to a light-emitting diode, and more particularly, to a light-emitting diode using quantum dots having different surface properties and a light-emitting device having the same.

Description of the Related Art

With advances in electron engineering and information technology, the technology of the display field for processing and displaying a large amount of information is also rapidly developing. Accordingly, various flat panel display devices replacing conventional cathode ray tubes (CRTs) have been developed. Among the flat display devices, an organic light-emitting diode (OLED) display device that can be formed in a thin film structure and has low power consumption is used as a next-generation display device that can replace a liquid crystal display (LCD) device.

However, when the current density or driving voltage of an OLED display device is increased to increase a luminance, due to deterioration of the OLED such as the degradation of an organic emissive material used in the OLED, the lifetime of the OLED becomes shorter. Particularly, OLEDs fail to implement a high level of color gamut required in ITU-R Recommendation BT.2020 (Rec. 2020 or BT.2020), which was developed by the International Telecommunication Union (ITU) in relation to the specification of 4K/UHD.

In recent years, efforts have been made to use quantum dots (QDs) in a display device. QDs are inorganic particles that emit light while electrons in an unstable state drop from a conduction band to a valence band. Among inorganic particles, QDs have a very high extinction coefficient and an excellent quantum yield, and thus emit strong fluorescence. In addition, since an emission wavelength varies according to a QD size, when the QD size is appropriately adjusted, light in the entire visible light region may be obtained, thereby realizing a variety of colors. That is, when QDs are used in an emitting material layer (EML), the color purity of each pixel may be increased, and since white light consisting of red (R), blue (B) and green (G) light with high purities may be realized, the Rec. 2020 standard may be satisfied.

A QD light-emitting diode (QLED) is developed using QDs. FIG. 1 illustrates a bandgap energy diagram in a general QLED. Referring to FIG. 1, the general QLED includes an anode and a cathode, which are disposed opposite each other, a QD-containing EML disposed between the anode and the cathode, a hole injection layer (HIL) and a hole transport layer (HTL) disposed between the anode and the EML, and an electron transport layer(ETL) disposed between the cathode and the EML.

The EML consists of nano-scale QDs, and is formed by, for example, applying a solution containing QDs in a solvent onto the HTL and then volatilizing the solvent. Meanwhile, the HIL and the HTL are configured to inject and transfer holes as a positive charge carrier from the anode to the EML, and the ETL is configured to inject and transfer electrons as a negative charge carrier from the cathode to the EML. To inject and transfer holes and electrons to the EML, it is necessary that each layer consist of a material having suitable bandgap energy. As an example, the HIL may consist of poly(3,4-ethylenedioxythiophene) polystyrene sulfonate (PEDOT:PSS), and the HTL may consist of poly (4-butylphenyl-diphenyl-amine) (poly-TPD), and the ETL may consist of ZnO.

QDs may be coated on the HTL by a solution process, and an organic ligand is bonded to a QD surface to uniformly disperse the QDs in a solvent used in the solution process. Conventionally, the organic ligand that binds to the QD surface has a functional group having a specific charge. Accordingly, a carrier having an opposite charge to the function group in the organic ligand may be rapidly transferred to the EML due to electrical attraction, whereas the transfer of a carrier having like charge to the functional group in the organic ligand to the EML is delayed by electrical repulsion.

As described above, since the injection of holes and electrons to the EML is not equilibrated in a conventional QLED, the electrons and the holes are not recombined at QDs in the EML. As a result, light emission occurs at the interface between the EML and a charge transfer layer, such as the HTL or the ETL, which is adjacent to the EML, and the luminous efficiency of the QLED is degraded. In addition, to drive the light-emitting diode, a high voltage has to be applied, and therefore, the driving voltage of the QLED is increased.

In addition, due to the van der Waals force formed between a ligand chain bonded to a QD surface and an organic solvent used in the synthesis of the QD, a large quantity of organic components remains in the EML coated with the finally synthesized QDs. Because of the large quantity of the organic components, it is difficult to uniformly control a thickness of the QD-containing EML. Moreover, as the organic components remaining in the EML penetrate into the ETL, which is adjacent to the EML, or into the cathode, the boundary between the layers becomes unclear, and therefore, it is difficult to form the ETL and the cathode.

BRIEF SUMMARY

Accordingly, the present disclosure is directed to a QLED and a light emitting display device including the same that obviate one or more of the problems due to limitations and disadvantages of the related art.

An object of the present disclosure is to provide a QLED which can be driven at low voltage and has improved luminous efficiency, and a QD light-emitting device including the same. One exemplary embodiment provides a quantum dot comprising a semiconductor nanocrystal or metal oxide core, a shell substantially or fully covering the core wherein the shell has an outer surface, an X-type ligand comprising a functional group selected from the group consisting of a carboxylate group, a phosphate group, and a thiolate group bound to a first region of the outer surface, and an L-type ligand comprising a functional group selected from the group consisting of an amino group, a thiol group, a phosphine group, and a phosphine oxide group bound to a second region of the outer surface.

In some embodiments. The first region and second region are respective hemispheres of the outer surface (e.g., wherein the outer surface is spherical in shape).

Another object of the present disclosure is to provide a QLED prepared by effectively controlling a thickness of an EML constituting the light-emitting diode and easily forming a charge transfer layer and an electrode, and a QD light-emitting device including the same.

According to an aspect of the present disclosure, the present disclosure provides a QLED, which includes first and second electrodes facing each other; and an EML between the first electrode and the second electrode and including QDs in which ligands are bonded to the QD surface, wherein the ligands include X-type ligands binding to a first region of the QD surface facing one electrode selected from the first electrode and the second electrode and L-type ligands binding to a second region of QD surface opposite to the first region.

The X-type ligand may bind to the first region of the QD through a negatively charged functional group selected from the group consisting of a carboxylate group, a phosphonate group and a thiolate group.

As an example, the X-type ligand may be derived from any one of $C_5$ to $C_{30}$ fatty acids.

The L-type ligand may bind to the second region of the QD through an unshared electron pair of a functional group selected from the group consisting of an amino group, a thiol group, a phosphine group and a phosphine oxide group.

As an example, the L-type ligand may be selected from the group consisting of $C_1$ to $C_{10}$ linear or branched alkyl amines, $C_4$ to $C_8$ alicyclic amines, $C_5$ to $C_{20}$ aromatic amines, $C_1$ to $C_{10}$ linear or branched alkyl phosphines, $C_1$ to $C_{10}$ linear or branched alkyl phosphine oxides and a combination thereof.

According to an exemplary embodiment, the QLED may further include a first charge transfer layer disposed between the first electrode and the EML, and a second charge transfer layer disposed between the second electrode and the EML.

In one exemplary embodiment, the first charge transfer layer may include a hole transfer layer, and the second charge transfer layer may include an electron transfer layer.

In this case, the X-type ligand may be provided at a part of the QD surface interfacing with the hole transfer layer, and the L-type ligand may be provided at a part of the QD surface interfacing with the electron transfer layer.

In another exemplary embodiment, the first charge transfer layer may include an electron transfer layer, and the second charge transfer layer may include a hole transfer layer.

In this case, the L-type ligand may be provided at a part of the QD surface interfacing with the electron transfer layer, and the X-type ligand may be provided at a part of the QD surface interfacing with the hole transfer layer.

According to another aspect of the present disclosure, the present disclosure provides a QD light-emitting device, which includes a substrate; the above-described QLED disposed on the substrate; and a driving element disposed between the substrate and the QLED and connected to the QLED.

As an example, the QD light-emitting device may include a QD light-emitting display device, but the present disclosure is not limited thereto.

BRIEF DESCRIPTION OF THE SEVERAL VIEWS OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

FIG. 2 shows QDs in which the negative charge of the X-type ligand is derived from a carboxylate, and an L-type ligand is bonded to the QD surface via a nitrogen atom constituting an amino group.

FIG. 4 is a cross-sectional view schematically illustrating an LED according to a second exemplary embodiment of the present disclosure, to which QDs in which different types of ligands are bonded to specific regions of the QD surface are applied. Provided below the cross-sectional view of the LED are the illustration of EMLs: one consisting of a monolayer of QDs, and the other consisting of a bilayer of QDs.

FIG. 9 is a graph illustrating a result of time-of-flight secondary ion mass spectrometry (TOF-SIMS) for QDs synthesized according to an exemplary embodiment of the present disclosure, in which different types of ligands are bonded to the QD surface.

FIG. 11A illustrates the cross-sectional structure of an EML and a charge transfer layer, and FIG. 11B illustrates the cross-sectional structure of an electrode. In addition, in FIGS. 11A and 11B, the image on the left shows an LED having an EML prepared by applying QDs synthesized according to a comparative example, in which only X-type ligands are bonded to the surface thereof, and the image on the right shows an LED having an EML prepared by applying QDs synthesized according to the present disclosure, in which different types of ligands are bonded to the QD surface.

DETAILED DESCRIPTION

Hereinafter, the present disclosure will be described with reference to the accompanying drawings when needed.

Figure 1:
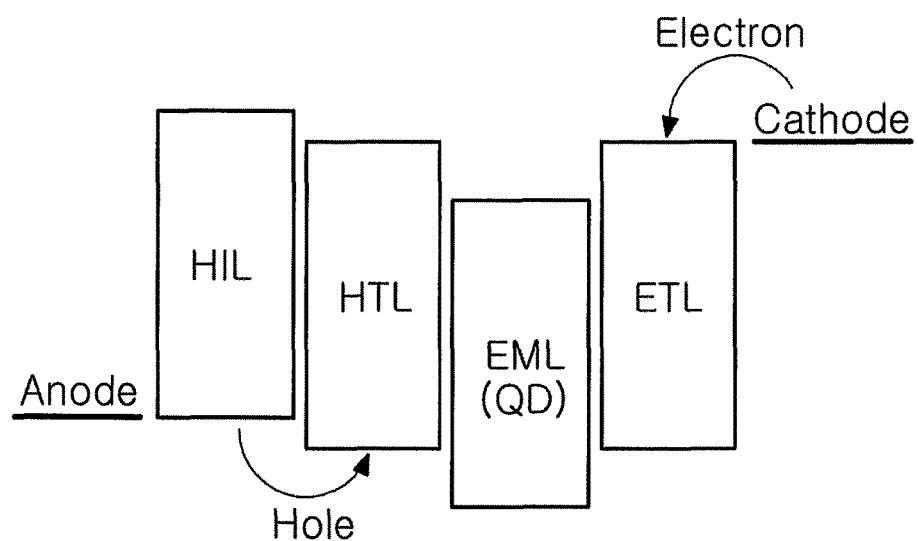
FIG. 1 is a schematic diagram illustrating bandgap energy of materials constituting an EML and a charge transfer layer in a general QLED.
Figure 2:
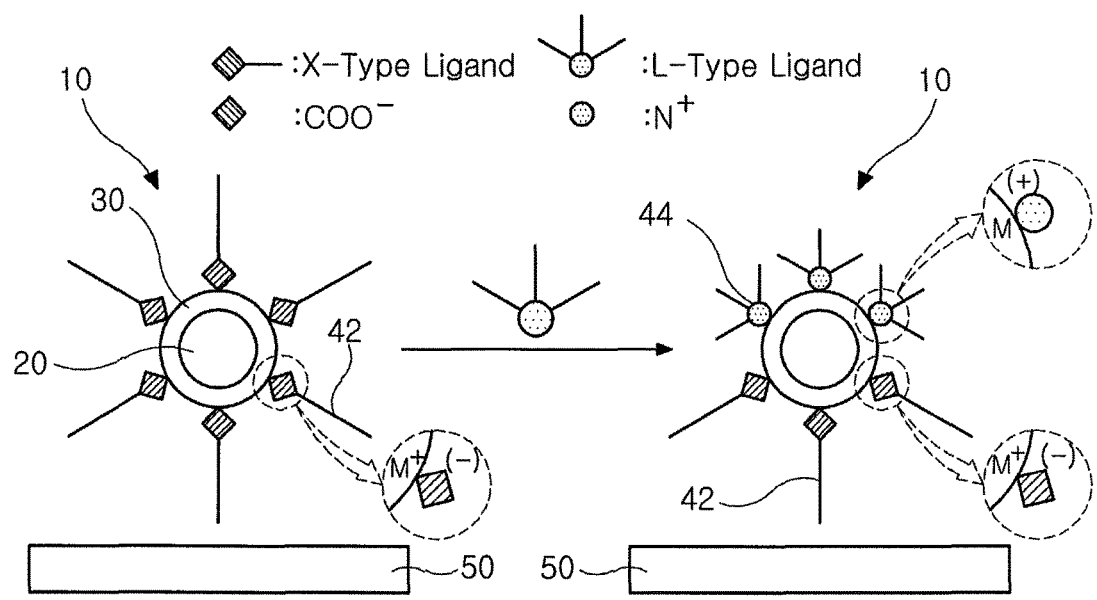
FIG. 2 is a schematic diagram illustrating the process of synthesizing a QD in which different types of ligands are bonded to corresponding regions of the QD surface, from a QD to which a single type of ligand is bonded.

According to an aspect of the present disclosure, the present disclosure relates to a QLED to which QDs in which ligands having different characteristics and/or types are bonded to specific regions of the QD surface are applied. FIG. 2 is a schematic diagram illustrating the process of synthesizing, from a QD in which a single type of ligands is bonded, a QD in which different types of ligands are bonded to specific regions of the QD surface.

As schematically illustrated in FIG. 2, according to the present disclosure, when a ligand exchange with L-type ligands 44 occurs from the QD 10A to which only X-type ligands 42 are bonded (left side of FIG. 2) to a part of the QD 10 surface, the QD 10 in which different types of ligands are bonded to different regions of the surface thereof may be synthesized. As an example, the right side of FIG. 2 shows the QD 10 having a spherical shape, in which X-type ligands 42 are bonded to the lower hemisphere of the QD surface and L-type ligands 44 are bonded to the upper hemisphere of the QD surface, which is opposite of where the X-type ligands 42 are bonded.

In one exemplary embodiment, the QD 10A shown on the left side of FIG. 2, in which only the X-type ligands 42 are bonded to the surface, may be synthesized by inputting a metal precursor (e.g., a fatty acid ester of a metal) corresponding to a cation of a core 20 into a high temperature reactor and performing pyrolysis or hot injection for dissolving the precursor, together with the fatty acid, in an organic solvent (e.g., octadecene having a high boiling point) (e.g., colloidal QDs). Meanwhile, when selenium (Se) or sulfur (S) is dissolved in an organic solvent such as alkyl phosphine (e.g., tri-butyl phosphine, tri-n-octyl phosphine, tris(trimethylsilyl)phosphine, etc.) and inputted into the reactor containing the dissolved metal precursor at a nucleation temperature, nucleation of the precursor occurs, and the reaction precursor which has not participated in the nucleation additionally reacts with a nuclear surface, resulting in the growth of a core 20.

Subsequently, a precursor of a shell 30 (e.g., a cationic metal precursor in which X-type ligands are bonded to the precursor surface and a sulfur precursor dissolved in alkyl phosphine) to be grown is additionally injected into the reactor containing the core 20 of the QD. Therefore, the QD 10A with a heterologous core 20/shell 30 structure in which the outer surface of the core 20 is surrounded by the shell 30 (an inorganic layer) in which X-type ligands 42 are bonded to the shell surface may be synthesized, without further nucleation. According to the reactivity and injection rates, a ligand type, a reaction temperature and the like of the reaction precursors constituting the core 20 and/or the shell 30, a degree of growth, a crystal structure and the like of the core 20/shell 30 constituting the QD 10A may be adjusted, and therefore, light emission in various wavelengths according to the adjustment of bandgap energy may be induced.

Here, the X-type ligand 42 in the entire surface region of the QD 10A refers to a negatively charged (−) organic ligand that binds to the surface of the QD 10A by a negatively charged functional group selected from the group consisting of, for example, a carboxylate group (—COO⁻), a phosphonate group and a thiolate group. In one exemplary embodiment, the X-type ligand 42 may bind to the surface of the QD 10A through a carboxylate group. Specifically, the X-type ligand 42 may be derived from a $C_5$ to $C_{30}$ saturated or unsaturated fatty acid, preferably a $C_8$ to $C_{20}$ saturated or unsaturated fatty acid. More specifically, the X-type ligand 42 may be derived from a saturated or unsaturated fatty acid such as an octanoic acid (caprylic acid, $CH_3(CH_2)_6COOH$), a decanoic acid ($CH_3(CH_2)_8COOH$), a dodecanoic acid (lauric acid, $CH_3(CH_2)_{10}COOH$), a myristic acid (1-tetradicanoic acid, $CH_3(CH_2)_{12}COOH$), palmitic acid (n-hexadecanoic acid, $CH_3(CH_2)_{14}COOH$), a stearic acid (n-octadecanoic acid, $CH_3(CH_2)_{16}COOH$), or an oleic acid (cis-9-octadecanoic acid, $(CH_3(CH_2)_7CH=CH(CH_2)_7COOH)$. In one embodiment, the X-type ligand 42 further comprises a $C_5$-$C_{30}$ saturated or unsaturated hydrocarbon chain. In more specific embodiment, the X-type ligand has one of the following structures:

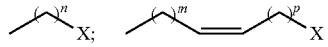

wherein n is an integer ranging from 6 to 16, m is an integer ranging from 4 to 9, p is an integer ranging from 4 to 9, and X is a carboxylate group, a phosphate group, or a thiolate group.

In this case, a negative charge, for example, a carboxylate group (—COO⁻), constituting the X-type ligand 42 is coupled with a metal cation (M⁺) constituting the shell 30 by a weak electrical interaction (M⁺:⁻OOC). When the QD 10A in which the negatively charged X-type ligands 42 are bonded to the surface thereof is used in an EML (see FIGS. 3 and 4) of a QD light-emitting diode (QLED; 100 and 200 in FIGS. 3 and 4, respectively), the following problems occur.

Since the X-type ligands 42 exhibit a negative charge, holes, i.e., positive charge carriers, may be rapidly injected and transferred to the surface of the QD 10A, which is a light emissive particle formed in an EML (see FIG. 3) by electrical attraction. On the other hand, the injection and transfer of electrons, i.e., negative charge carriers, which have the same charge as a charge formed in the X-type ligand 42, to the surface of the QD 10A formed in the EML (see FIG. 3) are delayed by electrical repulsion. Since the injection of the holes and the electrons is not equilibrated, the electrons and the holes are not recombined at the QD 10A in the EML, but are recombined at the interface between the EML (see FIG. 3) and an ETL 164 (see FIG. 3). Therefore, in the EML (see FIG. 3), an exciton is not sufficiently bonded but is quenched, and therefore the luminous efficiency of the light-emitting diode is degraded. In addition, since the application of a high voltage is required to drive the LED, the driving voltage of the LED is increased.

In addition, when the QD 10A is synthesized, an alkyl fatty acid is used as a source of the X-type ligand 42, and as a solvent, octadecene, an organic solvent, is used. Due to the strong van der Waals force between an alkyl chain constituting the fatty acid and octadecene, the solvent component is not completely removed. Therefore, in the QD 10A finally synthesized, in addition to the X-type ligand 42 component, a large quantity of organic components remains. When the EML (see FIG. 3) is formed of a coating of the QD 10A in which a large quantity of organic components remains, it is difficult to making a uniform coating of the QD 10A, and thus it is difficult to form an EML (see FIG. 3) with a uniform thickness.

Moreover, since a large quantity of the organic components remain in the EML (see FIG. 3), when a second charge transfer layer 160 (see FIG. 3) and a second electrode 120 (see FIG. 3) are stacked on a top surface of the EML (see FIG. 3), the remaining organic components penetrate into the second charge transfer layer, and/or the second electrode. Therefore, the boundaries within the second charge transfer layer and/or between the second charge transfer layer and the second electrode become(s) unclear, and the layers lose their original characteristics. For this reason, when the light-emitting diode 100 (see FIG. 3) is manufactured using the QD 10A in which the X-type ligand 42 is bonded to the entire QD surface, it is difficult to laminate a charge transfer layer (CTL) such as the second charge transfer layer 160 (see FIG. 3) and an electrode such as the second electrode 120 (see FIG. 3) with desired shapes or thicknesses.

Accordingly, in the present disclosure, a substrate 50 is coated with the QD 10A in which the X-type ligands 42, previously dispersed in an organic solvent, are bonded to the QD surface, and then the L-type ligands 44 are dispersed in a solvent. Since the L-type ligands 44 cannot react with, and a ligand exchange does not occur at a part blocked by the substrate 50 (the lower hemisphere region of the QD 10A surface in FIG. 2; first region), the X-type ligands 42 remain bonded to the above-described surface of the QD 10.

The L-type ligand 44 refers to a neutral organic ligand that binds to the surface of the QD 10 through an unshared electron pair. In one example, the L-type ligand 44 may bind to the QD surface through an unshared electron pair of a functional group selected from the group consisting of an amino group, a thiol group, a phosphine group and a phosphine oxide group. In one example, the L-type ligand 44 strongly binds to a metal cation (M$^+$; e.g., Zn$^+$) on the surface of the QD 10 by a coordination bond, which is shown below, using an unshared electron pair of a nitrogen atom (N) constituting an amino group.

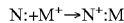

In an exemplary embodiment, the L-type ligand 44 may be a type of ligand which has completely or nearly no attraction caused by an interaction with an organic solvent (e.g., octadecene) used in the synthesis of the QD 10. In this case, since some X-type ligands 42 are replaced with the L-type ligands 44, the bonding between the QD and an organic component derived from the organic solvent is weakened, and thus the content of the organic components remaining in the finally synthesized QD 10 may be reduced.

For example, the L-type ligand 44 may be selected from the group consisting of $C_1$ to $C_{10}$ linear or branched alkyl amines (e.g., a monovalent, divalent or trivalent alkyl amine) and preferably $C_1$ to $C_5$ linear or branched alkyl amines, $C_4$ to $C_8$ alicyclic amines and preferably $C_5$ to $C_8$ alicyclic amines, $C_5$ to $C_{20}$ aromatic amines and preferably $C_5$ to $C_{10}$ aromatic amines, $C_1$ to $C_{10}$ linear or branched alkyl phosphines (e.g., a monovalent, divalent or trivalent alkyl phosphines) and preferably $C_1$ to $C_5$ linear or branched alkyl phosphines, $C_1$ to $C_{10}$ linear or branched alkyl phosphine oxides (e.g., a monovalent, divalent or trivalent alkyl phosphine oxide) and preferably $C_1$ to $C_5$ linear or branched alkyl phosphine oxides, and a combination thereof In one exemplary embodiment, the L-type ligands 44 include tertiary amines such as tris(2-aminoethy)amine (TAEA) and tris(2-aminomethyl)amine; alkyl polyamines such as N-butyl-N-ethylethane-1,2-diamine, ethylene diamine, and pentaethylenehexamine; alicyclic polyamines such as cyclohexane-1,2-diamine and cyclohexene-1,2-diamine; aromatic amines such as 2,3-diaminopyridine and a combination thereof, but the present disclosure is not limited thereto.

Unlike the X-type ligands 42 binding to the QD surface 10A by a weak electrical interaction (M$^+$:$^-$OOC), the L-type ligands 44 may strongly bind to the surface of the QD 10 by the coordination bond using unshared electron pairs. Accordingly, at the region of the QD surface 10A, which is not blocked by the substrate 50 (the upper hemisphere region of the QD surface 10A in FIG. 2; second region), a ligand exchange reaction is induced to replace the X-type ligands 42 weakly binding to the QD surface 10A with the L-type ligands 44 which strongly bind thereto. As a result of such a ligand exchange reaction, the QD 10 in which the X-type ligands 42 bind to the first surface region, and the L-type ligands 44 bind to the second surface region, which is an opposite part of the QD 10 surface to the first surface region, may be synthesized.

According to the present disclosure, the use of the QD 10 according to the present disclosure, in which the X-type ligand 42 exhibiting a negative charge bind to the first surface region of the surface of the QD 10, and the L-type ligands 44 exhibiting a positive charge bind to the second surface region, which is an opposite part of the QD 10 surface to the first surface region, to form the EML (see FIG. 3) brings the following advantages.

Holes, i.e., positive charge carriers, may be rapidly injected and transferred to the surface of the QD 10 in the EML (see FIG. 3) due to the electrical attraction with the X-type ligand 42, which is of an opposite charge, in the first surface region of the QD 10. Simultaneously, electrons, i.e., negative charge carriers, may be rapidly injected and transferred to the surface of the QD 10 in the EML (see FIG. 3) due to the electrical attraction with the L-type ligand 44, which is of an opposite charge, in the second surface region of the QD 10. Since the holes and the electrons are rapidly equilibrated and recombined at the QD 10 in the EML, quenching of excitons is reduced, and the luminous efficiency of the LED is enhanced. Since the recombination of excitons at the interface between the EML and an adjacent charge transfer layer (e.g., ETL), which is caused by the imbalanced injection of holes and electrons, is prevented, the LED may be driven at a low voltage.

In addition, when the X-type ligands 42 are removed from the QD 10 due to a ligand exchange between the X-type ligands 42 and the L-type ligands 44, the organic component (a component derived from an organic solvent such as octadecene) previously remained bound to the X-type ligands 42 due to the van der Waals force has a weaker van der Waals force with the L-type ligands 44. Accordingly, the organic component does not bind to the L-type ligands 44 and is removed from the surface of the QD 10. Since the content of the remaining organic components in the finally synthesized QD 10 is reduced, the QDs 10 may be uniformly applied to form the EML (see FIG. 3), and thus a thickness of the EML (see FIG. 3) may be uniformly controlled.

In addition, while the second charge transfer layer 160 (see FIG. 3) and the second electrode 120 (see FIG. 3) are stacked on a top surface of the EML (see FIG. 3), the organic components remaining in the EML do not penetrate into the second charge transfer layer and the second electrode. As the penetration of the organic components is prevented, the boundary between the second charge transfer layer and the second electrode may be clearly distinguished, and original characteristics of the layers may be maintained. Therefore, a CTL such as the second charge transfer layer 160 (see FIG. 3) and an electrode such as the second electrode 120 (see FIG. 3) may be stacked in desired shapes or thicknesses.

Next, the structure of the QD 10 synthesized according to the present disclosure will be described. In one exemplary embodiment, the QD 10 may have a homogeneous structure. In another exemplary embodiment, the QD 10 may have a heterologous structure including a core 20 and a shell 30. Here, the shell 30 may be one shell or multiple concentric shells.

As an example, the QD 10 may have a heterologous structure having: the core 20 disposed in the center of the QD 10 to emit light; and the shell 30 covering a surface of the core 20 to protect the core 20, and ligands 42 and 44 may cover a surface of the shell 30 to disperse the QD 10 in a solvent. For example, the QD 10 may have a type-I core/shell structure in which the energy bandgap of the component of the core 20 is surrounded by the energy bandgap of the shell 30, and electrons and holes are transferred to the core 20 and recombined in the core 20, which is a luminous matter, thereby emitting energy as light.

When the QDs 10 have a type-I core/shell structure, the core 20 is a part in which luminescence substantially occurs, and the emission wavelength of the QD 10 is determined according to the size (e.g., diameter) of the core 20. To take advantage of a quantum confinement effect, it is necessary that the core 20 has a smaller size than the exciton Bohr radius according to a material and has an optical bandgap in the corresponding size.

Meanwhile, the shell 30 constituting the QD 10 promotes the quantum confinement effect of the core 20 and determines the stability of the QD 10. Atoms exposed to the surface of the single-structured colloidal QDs 10, unlike internal atoms, have lone-pair electrons which do not participate in a chemical bond. Since energy levels of these surface atoms are located between the conduction band edge and the valence band edge of the QD 10, the surface atoms can trap the charges, thereby forming surface defects. Due to a non-radiative recombination process of excitons, caused by the surface defects, the luminous efficiency of the QDs 10 may be reduced, and the chemical composition of the QDs 10 may be modified by the reaction between the trapped charges and external oxygen and compound, or electrical/optical properties of the QDs 10 may be permanently lost.

Therefore, in one exemplary embodiment, the QD 10 may have a heterologous core 20/shell 30 structure. To effectively form the shell 30 on the surface of the core 20, it is necessary that the lattice constant of a material constituting the shell 20 be similar to that of a material constituting the core 20. As the surface of the core 20 is surrounded by the shell 30, the oxidation of the core 20 may be prevented, thereby enhancing the chemical stability of the QD 10. In addition, the loss of excitons caused by the surface trap on the surface of the core 20 may be minimized, and the loss of energy due to molecular vibration may be prevented, and thus a quantum yield may be enhanced.

The QD 10 may be a semiconductor nanocrystal or metal oxide particle exhibiting a quantum confinement effect. As an example, the QD 10 may include Group II-VI, III-V, IV-VI, and nano-semiconductor compounds. More specifically, the QD 10 may be a core 20/shell 30-structured nanocrystal in which each of the core 20 and/or shell 30 constituting the QD 10 may be a Group II-VI compound semiconductor nanocrystal such as CdS, CdSe, CdTe, ZnS, ZnSe, ZnTe, HgS, HgTe and/or a combination thereof; a Group III-V compound semiconductor nanocrystal such as GaP, GaAs, GaSb, InP, InAs, InSb and/or a combination thereof; a Group IV-VI compound semiconductor nanocrystal such as PbS, PbSe, PbTe and/or a combination thereof; a Group I-III-VI compound semiconductor nanocrystal such as $AgGaS_2$, $AgGaSe_2$, $AgGaTe_2$, $CuInS_2$, $CuInSe_2$, $CuGaS_2$, $CuGaSe_2$ and/or a combination thereof; a metal oxide nanoparticle such as ZnO, $TiO_2$ and/or a combination thereof; or CdSe/ZnSe, CdSe/ZnS, CdS/ZnSe, CdS/ZnS, ZnSe/ZnS, InP/ZnSZnO/MgO and/or an arbitrary combination thereof. The semiconductor nanoparticle may be undoped or doped with a rare earth element such as Eu, Er, Tb, Tm or Dy or an arbitrary combination thereof, or doped with a transition metal element such as Mn, Cu, Ag or Al or an arbitrary combination thereof.

For example, the core 20 of the QD 10 may be selected from the group consisting of ZnSe, ZnTe, CdSe, CdTe, InP, ZnCdS, $Cu_xIn_{1-x}S$, $Cu_xIn_{1-x}Se$, $Ag_xIn_{1-x}S$ and a combination thereof. In addition, the shell 30 of the QD 10 may be selected from the group consisting of ZnS, GaP, CdS, ZnSe, CdS/ZnS, ZnSe/ZnS, ZnS/ZnSe/CdSe, GaP/ZnS, CdS/CdZnS/ZnS, ZnS/CdSZnS, $Cd_xZn_{1-x}S$ and a combination thereof. Optionally, the QD 10 may be an alloy QD (e.g., $CdS_xSe_{1-x}$, $CdSe_xTe_{1-x}$, or $Zn_xCd_{1-x}Se$) such as a homogeneous alloy QD or a gradient alloy QD. In some embodiments, the QD has a substantially spherical shape, the surface region of which comprises two halves or two hemispheres, namely, a first hemisphere and a second hemisphere of the spherical shape. In some embodiments, the first region of the outer surface is the first hemisphere and the second region of the outer surface is the second hemisphere.

Figure 3:
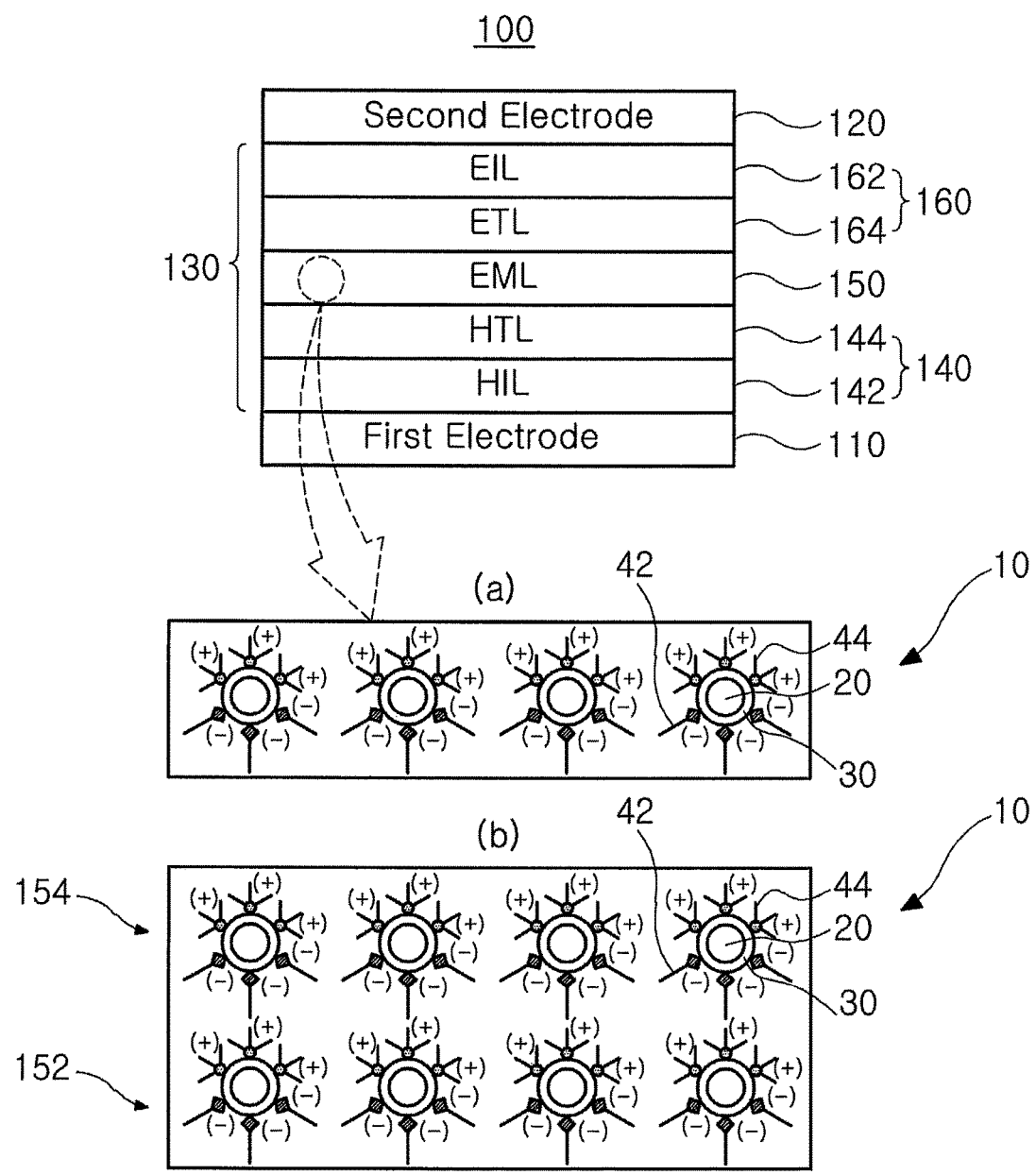
FIG. 3 is a cross-sectional view schematically illustrating a light-emitting diode (LED) according to a first exemplary embodiment of the present disclosure, which includes QDs in which different types of ligands are bonded to specific regions of the QD surface. Provided below the cross-sectional view of the LED are the illustration of EMLs: one consisting of a monolayer of QDs, and the other consisting of a bilayer of QDs.

Subsequently, an LED according to the present disclosure, which includes QDs in which different types of ligands are bonded to the QD surface, will be described. FIG. 3 is a cross-sectional view schematically illustrating an LED according to a first exemplary embodiment of the present disclosure, which includes QDs in which different types of ligands are bonded to specific regions of the QD surface. As shown in FIG. 3, the QLED 100 according to an exemplary embodiment of the present disclosure includes a first electrode 110, a second electrode 120 disposed opposite the first electrode 110, and an emissive layer 130 disposed between the first electrode 110 and the second electrode 120 and including an EML 150. As an example, the emissive layer 130 may further include a first charge transfer layer 140 disposed between the first electrode 110 and the EML 150, and a second charge transfer layer 160 disposed between the EML 150 and the second electrode 120.

In this exemplary embodiment, the first electrode 110 may be an anode such as a hole injection electrode. The first electrode 110 may be formed on a substrate formed of glass or a polymer (not shown in FIG. 3). As an example, the first electrode 110 may be a doped or undoped metal oxide such as indium-tin-oxide (ITO), indium-zinc-oxide (IZO), indium-tin-zinc oxide (ITZO), indium-copper-oxide (ICO), tin oxide ($SnO_2$), indium oxide ($In_2O_3$), cadmium:zinc oxide (Cd:ZnO), fluorine:tin oxide ($F:SnO_2$), indium:zinc oxide ($In:SnO_2$), gallium:tin oxide ($Ga:SnO_2$) or aluminum:zinc oxide (Al:ZnO; AZO). Optionally, the first electrode 110 may consist of a metal or nonmetal material containing nickel (Ni), platinum (Pt), gold (Au), silver (Ag), iridium (Ir) or a carbon nanotube (CNT), other than the above-described metal oxide.

In this exemplary embodiment, the second electrode 120 may be a cathode such as an electron injection electrode. As an example, the second electrode 120 may consist of Ca, Ba, Ca/Al, LiF/Ca, LiF/Al, BaF$_2$/Al, CsF/Al, CaCO$_3$/Al, BaF$_2$/Ca/Al, Al, Mg, Au:Mg or Ag:Mg. As an example, each of the first electrode 110 and the second electrode 120 may be stacked to have a thickness of 30 to 300 nm.

In one exemplary embodiment, in the case of a bottom emission-type LED, the first electrode 110 may consist of a transparent conductive metal such as ITO, IZO, ITZO or AZO, and the second electrode 120 may consist of Ca, Ba, Ca/Al, LiF/Ca, LiF/Al, BaF$_2$/Al, Al, Mg, or an Ag:Mg alloy.

The first charge transfer layer 140 is disposed between the first electrode 110 and the EML 150. In this exemplary embodiment, the first charge transfer layer 140 may be a hole transfer layer which provides holes to the EML 150. As an example, the first charge transfer layer 140 may include a HIL 142 disposed adjacent to the first electrode 110 between the first electrode 110 and the EML 150, and an HTL 144 disposed adjacent to the EML 150 between the first electrode 110 and the EML 150.

The HIL 142 facilitates the injection of holes from the first electrode 110 into the EML 150. As an example, the HIL 142 may consist of an organic material selected from the group consisting of poly(ethylenedioxythiophene):polystyrene sulfonate (PEDOT:PSS), 4,4',4"-tris(diphenylamino)triphenylamines (TDATA) doped with tetrafluoro-tetracyano-quinodimethane (F4-TCNQ), a p-doped phthalocyanine (e.g., F4-TCNQ-doped zinc phthalocyanine (ZnPc)), F4-TCNQ-doped N,N'-diphenyl-N,N'-bis(1-naphtyl)-1,1'-biphenyl-4,4"-diamine (α-NPD), hexaazatriphenylene-hexanitrile (HAT-CN), and a combination thereof, but the present disclosure is not limited thereto. As an example, the dopant such as F4-TCNQ may be used for doping of a host at 1 to 30 wt % with respect to the weight of the host. The HIL 142 may be omitted according to the structure and type of the light-emitting diode 100.

The HTL 144 transports holes from the first electrode 110 to the EML 150. The HTL 144 may consist of an inorganic material or an organic material. As an example, when the HTL 144 consists of an organic material, the HTL 144 may consist of an organic material selected from the group consisting of aryl amines such as 4,4'-N,N'-dicarbazolyl-biphenyl (CBP), N,N'-diphenyl-N,N'-bis(1-naphtyl)-1,1'-biphenyl-4,4"-diamine (α-NPD), N,N'-diphenyl-N,N'-bis(3-methylphenyl)-(1,1'-biphenyl)-4,4'-diamine (TPD), N,N'-bis(3-methylphenyl)-N,N'-bis(phenyl)-spiro (spiro-TPD), N,N'-di(4-(N,N'-diphenyl-amino)phenyl)-N,N'-diphenyl-benzidine (DNTPD), 4,4',4"-tris(N-carbazolyl)-triphenylamine (TCTA), tris(3-methylphenylphenylamino)-triphenylamine (m-MTDATA), poly[(9,9'-dioctylfluorenyl-2,7-diyl)-co-(4,4'-(N-(4-sec-butylphenyl)diphenylamine))] (TFB), and poly(-butylphenyl-diphenyl amine) (poly-TPD); a polyaniline; a polypyrrole; poly(para)phenylenevinylenes and derivatives thereof such as poly(phenylenevinylene) (PPV), poly[2-methoxy-5-(2-ethylhexyloxy)-1,4-phenylenevinylene] (MEH-PPV) and poly[2-methoxy-5-(3',7'-dimethyloctyloxy)-1,4-phenylenevinylene] (MOMO-PPV); copper phthalocyanine; aromatic tertiary amines or polynuclear aromatic tertiary amines; a 4,4'-bis(p-carbazolyl)-1,1'-biphenyl compound; N,N,N',N'-tetraarylbenzidine; PEDOT:PSS and derivatives thereof; poly(N-vinylcarbazole) (PVK) and derivatives thereof; a polymethacrylate and derivatives thereof; poly(9,9-octylfluorene) and derivatives thereof; poly(spiro-fluorene) and derivatives thereof; N,N'-di(naphthalene-1-yl)-N,N'-diphenyl-benzidine (NPB); Spiro-NPB; and a combination thereof.

When the HTL 144 consists of an inorganic material, the HTL 144 may consist of an inorganic material selected from the group consisting of a metal oxide such as NiO, MoO$_3$, Cr$_2$O$_3$, Bi$_2$O$_3$ or p-type ZnO; non-oxidized equivalents such as copper thiocyanate (CuSCN), Mo$_2$S, or p-type GaN; and a combination thereof While the first charge transfer layer 140 is divided into the HIL 142 and the HTL 144 in FIG. 3, the first charge transfer layer 140 may be formed as a monolayer. For example, the first charge transfer layer 140 may only consisting of the HTL 144 without the HIL 142, or may be formed by doping the above-described hole-transporting organic material with a hole injection material (e.g., PEDOT:PSS).

The first charge transfer layer 140 including the HIL 142 and the HTL 144 may be formed by one process selected from vacuum deposition processes such as vacuum vapor deposition and sputtering, and solution processes such as spin coating, drop coating, dip coating, spray coating, roll coating, flow coating, casting, screen printing and inkjet printing; or a combination of these processes. For example, thicknesses of the HIL 142 and the HTL 144 may be 10 to 200 nm, and preferably 10 to 100 nm, but the present disclosure is not limited thereto.

The EML 150 may be a layer filled with the electroluminescent nanoparticles according to the present disclosure, that is, the QDs 10. The QDs 10 may be formed in a heterologous structure consisting of a core 20, which is a luminous matter, and a shell 30 surrounding the core 20, and different types of ligands 42 and 44 may bind to the surface of the shell 30. Here, the EML 150 may consist of a monolayer of the QDs 10 as shown in FIG. 3(a), or a multilayer, including two or more layers, of the QDs 10 as shown in FIG. 3(b).

In one exemplary embodiment, the EML 150 may be formed by applying a dispersion containing the electroluminescent nanoparticles (i.e., QDs 10) in a solvent on the first charge transfer layer 140 using a solution process, and volatilizing the solvent. The EML 150 may be formed using one selected from the solution processes such as spin coating, drop coating, dip coating, spray coating, roll coating, flow coating casting, screen printing and inkjet printing, or a combination thereof.

In one exemplary embodiment, the EML 150 may include electroluminescent nanoparticles (i.e., QDs 10) which have photoluminescence (PL) characteristics at 440 nm, 530 nm and 620 nm, thereby manufacturing a white LED. Optionally, the EML 150 may include electroluminescent nanoparticles (i.e., QDs 10) emitting any one of red, green and blue lights, wherein the QDs 10 may each independently emit light of any one of the colors.

As described above, the different types of ligands 42 and 44 may bind to the surface of the QD 10. In this exemplary embodiment, the X-type ligands 42 having a negatively charged functional group are positioned at a part of the surface of the QD 10 facing the first electrode 110, involved in injection and transfer of holes, i.e., carriers of an opposite charge to that of the X-type ligand 42. That is, the X-type ligands 42 are positioned to face the interface between the EML 150 and the first charge transfer layer 140. In addition, the L-type ligands 44 having a positively charged functional group are positioned at a part of the QD 10 facing the second electrode 120, involved in injection and transfer of electrons, i.e., carriers of an opposite charge to that of the L-type ligand 44. That is, the L-type ligands 44 are positioned to face the interface between the EML 150 and the second charge transfer layer 160.

Meanwhile, the second charge transfer layer 160 is disposed between the EML 150 and the second electrode 120. In this exemplary embodiment, the second charge transfer layer 160 may be an electron transfer layer which provides an electron to the EML 150. In one exemplary embodiment, the second charge transfer layer 160 may include an electron injection layer (EIL) 162 disposed adjacent to the second electrode 120 between the second electrode 120 and the EML 150, and an ETL 164 disposed adjacent to the EML 150 between the second electrode 120 and the EML 150.

The ETL 162 is configured to easily inject electrons from the second electrode 120 into the EML 150. For example, the EIL 162 may consist of a material in which a metal such as Al, Cd, Cs, Cu, Ga, Ge, In or Li is doped or bound with fluorine, or of a metal oxide (e.g., titanium dioxide ($TiO_2$), zinc oxide (ZnO), zirconium oxide (ZrO), tin oxide ($SnO_2$), tungsten oxide ($WO_3$) or tantalum oxide ($Ta_2O_3$)) which is undoped or doped with Al, Mg, In, Li, Ga, Cd, Cs, Cu or the like.

The ETL 164 is configured to transport electrons to the EML 150. The ETL 164 may consist of an inorganic material and/or an organic material. The ETL 164 may consist of an inorganic material selected from the group consisting of metal/non-metal oxides (e.g., titanium dioxide ($TiO_2$), zinc oxide (ZnO), zirconium oxide (ZrO), tin oxide ($SnO_2$), tungsten oxide ($WO_3$), tantalum oxide ($Ta_2O_3$), hafnium oxide ($HfO_3$), aluminum oxide ($Al_2O_3$), zirconium silicon oxide ($ZrSiO_4$), barium titanium oxide ($BaTiO_3$), and barium zirconium oxide ($BaZrO_3$)), which are undoped or doped with Al, Mg, In, Li, Ga, Cd, Cs or Cu; semiconductor particles (e.g., CdS, ZnSe and ZnS), which are undoped or doped with Al, Mg, In, Li, Ga, Cd, Cs or Cu; a nitride such as $Si_3N_4$; and a combination thereof.

Alternatively, the ETL 164 may consist of an organic material selected from the group consisting of an oxazole-based compound, an isooxazole-based compound, a triazole-based compound, an isothiazole-based compound, an oxadiazole-based compound, a thiadiazole-based compound, a phenanthroline-based compound, a perylene-based compound, a benzoxazole-based compound, a benzothiazole-based compound, a benzimidazole-based compound, a triazine-based compound, and an aluminum complex. Specifically, the organic material that can be used to form the ETL 164 may be selected from the materials including 3-(biphenyl-4-yl)-5-(4-tertbutylphenyl)-4-phenyl-4H-1,2,4-triazole (TAZ), bathocuproine (2,9-dimethyl-4,7-diphenyl-1,10-phenanthroline; BCP), 2,2',2"-(1,3,5-benzinetriyl)-tris(1-phenyl-1-H-benzimidazole); TPBi), tris(8-hydroxyquinoline)aluminum ($Alq_3$), bis(2-methyl-8-quninolinato)-4-phenylphenolatealuminum (III) (Balq), bis(2-methyl-quinolinato)(triphenylsiloxy) aluminum (III) (Salq) and a combination thereof, but the present disclosure is not limited thereto.

Similar to the first charge transfer layer 140, although FIG. 3 illustrates the second charge transfer layer 160 as a bilayer including the EIL 162 and the ETL 164, the second charge transfer layer 160 may be formed as a monolayer of the ETL 164. In addition, the second charge transfer layer 160 may be formed as a monolayer of an ETL 164 formed of a blend of cesium carbonate with the above-described electron-transporting inorganic material.

The second charge transfer layer 160 including the EIL 162 and/or the ETL 164 may be formed using one selected from solution processes such as spin coating, drop coating, dip coating, spray coating, roll coating, flow coating, casting, screen printing and inkjet printing, or a combination thereof. As an example, each of the ETL 162 and the ETL 164 may be stacked to a thickness of 10 to 200 nm, and preferably, 10 to 100 nm.

For example, when a hybrid CTL in which the HTL 144 of the first charge transfer layer 140 is formed of an organic material, and the second charge transfer layer 160 is formed of an inorganic material, or in which the HTL 144 is formed of an inorganic material, and the second charge transfer layer 160 is formed of an organic material is introduced, luminescence characteristics of the QLED 100 may be enhanced.

Meanwhile, when holes are transferred to the second electrode 120 through the EML 150 or electrons are transported to the first electrode 110 through the EML 150, the lifespan and efficiency of the diode may be reduced. To prevent such reduction, the QLED 100 according to an exemplary embodiment of the present disclosure may include at least one exciton blocking layer disposed adjacent to the EML 150.

For example, the QLED 100 according to an exemplary embodiment of the present disclosure may include an electron blocking layer (EBL) capable of controlling and preventing the transfer of electrons between the HTL 144 and the EML 150.

As an example, the EBL may consist of TCTA, tris[4-(diethylamino)phenyl]amine), N-(biphenyl-4-yl)-9,9-dimethyl-N-(4-(9-phenyl-9H-carbazole-3-yl)phenyl)-9H-fluorene-2-amine, tri-p-tolylamine, 1,1-bis(4-(N,N'-di(p-tolyl) amino)phenyl)cyclohexane (TAPC), m-MTDATA, 1,3-bis (N-carbazolyl)benzene (mCP), 3,3'-bis(N-carbazolyl)-1,1'-biphenyl (mCBP), poly-TPD, copper phthalocyanine (CuPc), DNTPD and/or 1,3,5-tris[4-(diphenylamino)phenyl]benzene (TDAPB).

In addition, a hole blocking layer (HBL), as a second exciton blocking layer, may be disposed between the EML 150 and the ETL 164, thereby preventing the transfer of holes between the EML 150 and the ETL 164. In one exemplary embodiment, a material for the HBL may be a derivative of an oxadiazole-based compound, a triazole-based compound, a phenanthroline-based compound, a benzoxazole-based compound, a benzothiazole-based compound, a benzimidazole-based compound, a triazine-based compound or the like, which may be used in the ETL 164.

For example, the HBL may consist of 2,9-dimethyl-4,7-diphenyl-1,10-phenanthroline (BCP), BAlq, Alq3, PBD, spiro-PBD and/or Liq, which have/has a deeper highest occupied molecular orbital (HOMO) energy level than that of the material used for the EML 150.

As described above, according to this exemplary embodiment, different types of ligands bind to the surface of the QD 10, which is an electroluminescent nanoparticle constituting the EML 150. In the EML 150, the X-type ligands 42 which exhibit a negative charge are positioned at a part of the QD surface facing the first electrode 110 involved in generation, injection and transfer of holes exhibiting an opposite charge to that of the X-type ligand 42. Specifically, the X-type ligands 42 are positioned to face the interface between the EML 150 and the HTL 144 in the first charge transfer layer 140. On the other hand, in the EML 150, the L-type ligands 44 exhibiting a positive charge are positioned at a part of the QD surface facing the second electrode 120 involved in generation, injection and transfer of electrons exhibiting an opposite charge to that of the L-type ligand 44. Specifically, the L-type ligands 44 are positioned to face the interface between the EML 150 and the ETL 164 in the second charge transfer layer 160.

Holes, i.e., positive charge carriers, may be rapidly transported to the surface of the QD 10 constituting the EML 150, due to the X-type ligands 42 exhibiting an opposite charge to that of the holes. Simultaneously, electrons, which are negative charge carriers, may be rapidly transported to the surface of the QD 10 applied in the EML 150, due to the L-type ligands 44 exhibiting an opposite charge to that of the electrons. As the holes and the electrons are equilibrated, and rapidly recombined in the EML 150, the light-emitting diode 100 may have enhanced luminous efficiency and may be driven at a low voltage.

In addition, since the L-type ligands 44 having no interaction with an organic component bind to the surface of the QD 10 by replacing the X-type ligands 42, a smaller quantity of organic components remains with the QD 10 according to the present disclosure, compared with the QD 10A consisting only of the X-type ligands 42 (see FIG. 2). Accordingly, the QDs 10 may be uniformly applied, and thereby the EML 150 may be controlled to have a uniform thickness. In addition, when the second charge transfer layer 160 and the second electrode 120 are stacked on the EML 150, the organic components do not penetrate into the second charge transfer layer 160 and the second electrode 120. Therefore, the boundary between the second charge transfer layer 160 and the second electrode 120 may be clearly distinguished, and the second charge transfer layer 160 and the second electrode 120 may be formed with desired shapes or thicknesses.

Meanwhile, in FIG. 3, the QLED having a normal structure, in which the HTL is disposed between the first electrode having a relatively low work function and the EML, and the ETL is disposed between the second electrode having a relatively high work function and the EML, was illustrated. The QLED may have an inverted structure, rather than the normal structure, as will be described.

FIG. 4 is a cross-sectional view schematically illustrating a QLED having an inverted structure according to a second exemplary embodiment of the present disclosure, to which QDs in which different types of ligands are bonded to specific regions of the QD surface are applied. As shown in FIG. 4, the QLED 200 according to the exemplary embodiment of the present disclosure includes a first electrode 210, a second electrode 220 disposed opposite the first electrode 210, and an emissive layer 230 disposed between the first electrode 210 and the second electrode 220 and including an EML 250. The emissive layer 230 may further include a first charge transfer layer 240 disposed between the first electrode 210 and the EML 250, and a second charge transfer layer 260 disposed between the second electrode 220 and the EML 250.

The first electrode 210 may be a cathode such as an electron injection electrode. As an example, the first electrode 210 may consist of a doped or undoped metal oxide such as ITO, IZO, ITZO, ICO, $SnO_2$, $In_2O_3$, Cd:ZnO, F:$SnO_2$, In: $SnO_2$, Ga: $SnO_2$ and AZO, or of a material containing Ni, Pt, Au, Ag, Ir or a CNT, other than the above-described metal oxide.

The second electrode 220 may be an anode such as a hole injection electrode. As an example, the second electrode 220 may be Ca, Ba, Ca/Al, LiF/Ca, LiF/Al, $BaF_2$/Al, CsF/Al, $CaCO_3$/Al, $BaF_2$/Ca/Al, Al, Mg, Au:Mg or Ag:Mg. For example, each of the first electrode 210 and the second electrode 220 may be stacked to a thickness of 30 to 300 nm.

In this exemplary embodiment, the first charge transfer layer 240 may be an electron transfer layer which provides an electrode to the EML 250. In one exemplary embodiment, the first charge transfer layer 240 includes an ETL 242 disposed adjacent to the first electrode 210 between the first electrode 210 and the EML 250, and an ETL 244 disposed adjacent to the EML 250 between the first electrode 210 and the EML 250.

The EIL 242 may consist of a material in which a metal such as Al, Cd, Cs, Cu, Ga, Ge, In or Li is doped or bound with fluorine, or of a metal oxide (e.g., $TiO_2$, ZnO, ZrO, $SnO_2$, $WO_3$, or $Ta_2O_3$), which is undoped or doped with Al, Mg, In, Li, Ga, Cd, Cs or Cu.

The ETL 244 may consist of an inorganic material and/or an organic material. When the ETL 244 is formed of an inorganic material, the ETL 244 may be formed of an inorganic material selected from the group consisting of metal/non-metal oxides such as $TiO_2$, ZnO, ZrO, $SnO_2$, $WO_3$, $Ta_2O_3$, $HfO_3$, $Al_2O_3$, $ZrSiO_4$, $BaTiO_3$, and $BaZrO_3$, which are undoped or doped with Al, Mg, In, Li, Ga, Cd, Cs or Cu; semiconductor particles such as CdS, ZnSe and ZnS, which are undoped or doped with Al, Mg, In, Li, Ga, Cd, Cs or Cu; a nitride such as $Si_3N_4$, and a combination thereof When the ETL 244 is formed of an organic material, the ETL 244 may be formed of an organic material such as an oxazole-based compound, an isooxazole-based compound, a triazole-based compound, an isothiazole-based compound, an oxadiazole-based compound, a thiadiazole-based compound, a perylene-based compound or an aluminum complex. Specifically, the organic material that can be used to form the ETL 244 may be an organic material selected from the group consisting of TAZ, BCP, TPBi, $Alq_3$, Balq, Salq and a combination thereof, but the present disclosure is not limited thereto.

The first charge transfer layer 240 may be formed as a monolayer only of the ETL 244. Alternatively, the first charge transfer layer 240 may be formed as a monolayer of the ETL 244 formed by blending cesium carbonate with the above-described electron-transporting inorganic material. As an example, each of the EIL 242 and the ETL 244 may be stacked to a thickness of 10 to 200 nm, preferably, 10 to 100 nm.

The EML 250 may be a layer filled with the electroluminescent nanoparticles according to the present disclosure, that is, the QDs 10. The QDs 10 may be formed in a heterologous structure consisting of a core 20, which is a luminous matter, and a shell 30 surrounding the core 20, and two different types of ligands 42 and 44 may bind to the surface of the shell 30. Here, the EML 250 may be formed as a monolayer of the QDs 10 as shown in FIG. 4A, or as a multilayer including two or more layers, of the QDs 10 as shown in FIG. 4B.

In one exemplary embodiment, the EML 250 may be formed by applying, a dispersion containing the electroluminescent nanoparticles (i.e., QDs 10) in a solvent on the first charge transfer layer 240 by a solution process and volatilizing the solvent.

As described above, two different types of the ligands 42 and 44 may bind to the surface of the QD 10. In this exemplary embodiment, the X-type ligands 42 having a negatively-charged functional group are positioned at a part of the QD 10 surface facing the second electrode 220, involved in injection and transfer of holes, i.e., carriers of an opposite charge to that of the X-type ligand 42. That is, the X-type ligands 42 are positioned to face the interface between the EML 250 and the second charge transfer layer 260. In addition, the L-type ligands 44 having a positively-charged functional group are positioned at a part of the QD 10 surface facing the first electrode 210, involved in injection and transfer of electrons, i.e., carriers of an opposite charge to that of the L-type ligand 44. That is, the L-type ligands 44 are positioned to face the interface between the EML 250 and the first charge transfer layer 240.

Meanwhile, in this exemplary embodiment, the second charge transfer layer 260 may be a hole transfer layer that provides holes to the EML 250. In one exemplary embodiment, the second charge transfer layer 260 may include a HIL 262 disposed adjacent to the second electrode 220 between the second electrode 220 and the EML 250, and an HTL 264 disposed adjacent to the EML 250 between the second electrode 220 and the EML 250.

The HIL 262 may be formed of a material selected from the group consisting of PEDOT:PSS, F4-TCNQ-doped TDATA, such as a p-doped phthalocyanine (e.g., F4-TCNQ-doped ZnPc), F4-TCNQ-doped α-NPD, HAT-CN and a combination thereof, but the present disclosure is not limited thereto. As an example, a dopant such as F4-TCNQ may be used for doping of a host at a quantity of 1 to 30 wt % with respect to the weight of a host. The HIL 262 may be omitted according to the structure and type of the light-emitting diode 200.

The HTL 264 may consist of an inorganic material or an organic material. As an example, the HTL 264 may consist of an organic material selected from the group consisting of aryl amines such as CBP, α-NPD, TPD, spiro-TPD, DNTPD, TCTA, m-MTDATA, TFB and poly-TPD; a polyaniline; a polypyrrole; poly(para)phenylenevinylenes such as PPV, MEH-PPV and MOMO-PPV and derivatives thereof; copper phthalocyanine; aromatic tertiary amines or polynuclear tertiary amines; 4,4'-bis(p-carbazolyl)-1,1'-biphenyl compounds; N,N,N',N'-tetraarylbenzidine; PEDOT:PSS and derivatives thereof; poly-N-vinylcarbazole and derivatives thereof; polymethacrylate and derivatives thereof; poly(9,9-octylfluorene) and derivatives thereof; poly(spiro-fluorene) and derivatives thereof; NPB; Spiro-NPB and a combination thereof.

The HTL 264 may consist of an inorganic material selected from the group consisting of metal oxides such as NiO, $MoO_3$, $Cr_2O_3$, $Bi_2O_3$ and p-type ZnO; non-oxidized equivalents such as copper thiocyanate (CuSCN), $Mo_2S$, and p-type GaN; and a combination thereof.

The second charge transfer layer 260 may be formed as a monolayer. For example, the second charge transfer layer 260 may consist of only the HTL 264 without the HIL 262, or may be prepared by doping the above-described hole-transporting organic material with a hole injection material (e.g., PEDOT:PSS). Thicknesses of the HIL 262 and the HTL 264 may range from 10 to 200 nm, and preferably 10 to 100 nm, but the present disclosure is not limited thereto.

Similar to the first exemplary embodiment, the QLED 200 according to the second exemplary embodiment of the present disclosure may include at least one exciton blocking layer disposed adjacent to the EML 250. For example, the QLED 200 may further include an EBL disposed between the EML 250 and the HTL 264 to control and prevent the transfer of electrons, and an HBL disposed between the ETL 244 and the EML 250 to control and prevent the transfer of holes.

As described above, according to this exemplary embodiment, different types of ligands bind to the surface of the QD 10, which is the electroluminescent nanoparticle constituting the EML 250. In the EML 250, the X-type ligands 42 which exhibit a negative charge are positioned at a part of the QD surface facing the second electrode 220, involved in generation, injection and transfer of holes exhibiting an opposite charge to that of the X-type ligand 42. Specifically, the X-type ligands 42 are positioned to face the interface between the EML 250 and the HTL 264 in the second charge transfer layer 260. On the other hand, in the EML 250, the L-type ligands 44 exhibiting a positive charge are positioned at a part of the QD surface facing the first electrode 210, involved in generation, injection and transfer of electrons exhibiting an opposite charge to that of the L-type ligand 44. Specifically, the L-type ligands 44 are positioned to face the interface between the EML 250 and the ETL 244 in the first charge transfer layer 240.

Holes, i.e., positive charge carriers, and electrons, i.e., negative charge carriers, are rapidly transferred to the surface of the QD 10 applied in the EML 250 due to the X-type ligands 42 and the L-type ligands 44, which have opposite charges to each other. Since the holes and the electrons are equilibrated and rapidly recombined in the EML 250, the light-emitting diode 200 may have enhanced luminous efficiency and may be driven at a low voltage.

In addition, since, since the L-type ligands 44 having no interaction with an organic component bind to the surface of the QD 10 by replacing the X-type ligands 42, a smaller quantity of organic components remains with the QD 10 according to the present disclosure. Accordingly, the QDs 10 may be uniformly applied, and thereby the EML 250 may be controlled to have a uniform thickness. In addition, when the second charge transfer layer 260 and the second electrode 220 are stacked on the EML 250, the organic components do not penetrate into the second charge transfer layer 260 and the second electrode 220. Therefore, the boundary between the second charge transfer layer 260 and the second electrode 220 may be clearly distinguished, and the second charge transfer layer 260 and the second electrode 220 may be formed with desired shapes or thicknesses.

Figure 5:
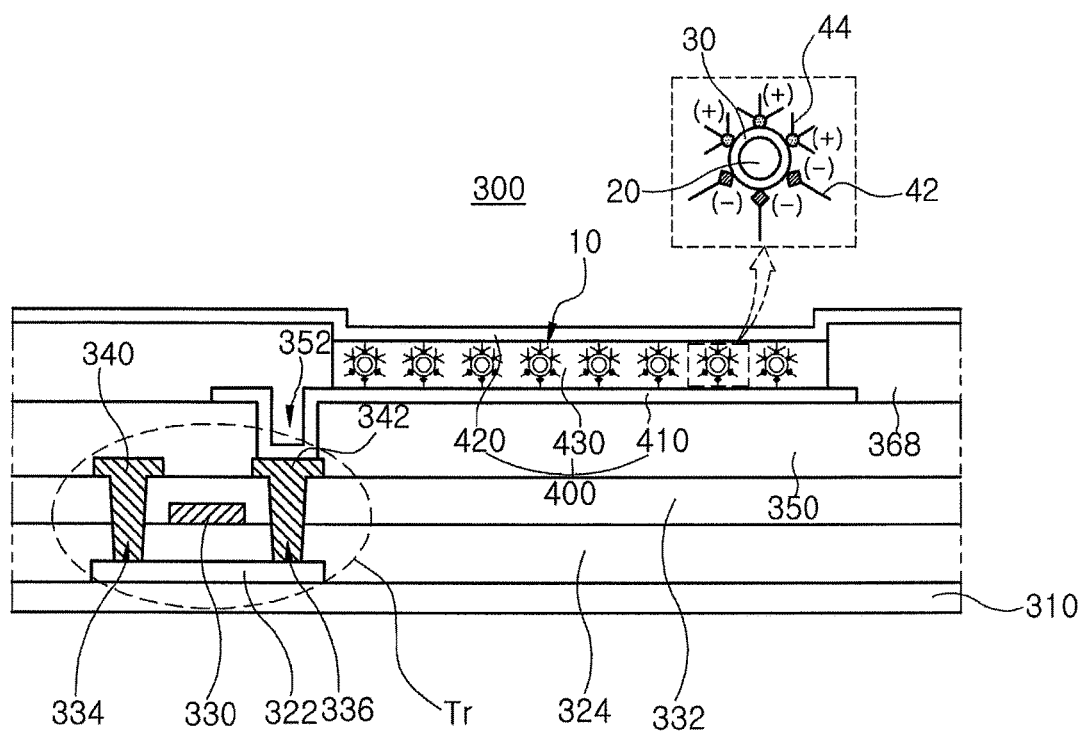
FIG. 5 is a cross-sectional view of a quantum dot light-emitting device as an example of a light-emitting device including an LED according to an exemplary embodiment of the present disclosure.

Therefore, the QLED in which the QD 10 as an electroluminescent nanoparticle according to the present disclosure in which different types of the ligands 42 and 44 bind to two distinguished regions of the QD surface, is used in the emissive layer may be applied to a light-emitting device such as a lighting device or a display device. As an example, a QD light-emitting display device having the QLED in which the QD 10, which is the electroluminescent nanoparticle according to the present disclosure, is used in the emissive layer will be described. FIG. 5 is a cross-sectional view of a QD light-emitting device according to an exemplary embodiment of the present disclosure.

As shown in FIG. 5, the QD light-emitting display device 300 includes a substrate 310, a driving thin film transistor Tr, which is a driving element, disposed on the substrate 310, and a QLED 400 connected to the driving thin film transistor Tr.

A semiconductor layer 322 consisting of an oxide semiconductor material or polycrystalline silicon is formed on the substrate 310. When the semiconductor layer 322 consists of an oxide semiconductor material, a light screening pattern (not shown) may be formed under the semiconductor layer 322 to prevent light from being incident upon the semiconductor layer 322, thus preventing degradation of the semiconductor layer 322 due to light. In contrast, the semiconductor layer 322 may consist of polycrystalline silicon, and in this case, opposite edges of the semiconductor layer 322 may be doped with impurities.

A gate insulating film 324 consisting of an insulating material is formed on the semiconductor layer 322. The gate insulating film 324 may consist of an inorganic insulating material such as silicon oxide ($SiO_2$) or silicon nitride (SiNx). A gate electrode 330 consisting of a conductive material such as a metal is formed on the gate insulating film 324 to correspond to the center of the semiconductor layer 322.

An interlayer insulating film 332 consisting of an insulating material is formed on the gate electrode 330. The interlayer insulating film 332 may be formed of an inorganic insulating material such as silicon oxide ($SiO_2$) or silicon nitride (SiNx), or an organic insulating material such as benzocyclobutene or photo-acryl.

The interlayer insulating film 332 has first and second semiconductor layer contact holes 334 and 336 exposing two opposite sides of the semiconductor layer 322. The first and second semiconductor layer contact holes 334 and 336 are disposed on either side of the gate electrode 330 such that they are spaced apart from the gate electrode 330. A source electrode 340 and a drain electrode 342, which consist of a conductive material such as a metal, are formed on the interlayer insulating film 332.

The source electrode 340 and the drain electrode 342 are disposed on either side of the gate electrode 330 such that they are spaced apart from the gate electrode 330, and are connected to two opposite sides of the semiconductor layer 322 via the first and second semiconductor layer contact holes 334 and 336.

The semiconductor layer 322, the gate electrode 330, the source electrode 340, and the drain electrode 342 together constitute the driving thin film transistor Tr, which is a driving element.

In FIG. 5, the driving thin film transistor Tr has a coplanar structure in which the gate electrode 330, the source electrode 340 and the drain electrode 342 are disposed on the semiconductor layer 322. Alternatively, the driving thin film transistor Tr may have an inverted staggered structure in which a gate electrode is disposed under the semiconductor layer, and a source electrode and a drain electrode are disposed on the semiconductor layer. In this case, the semiconductor layer may consist of amorphous silicon.

Although not shown in FIG. 5, pixel areas are defined by gate lines and data lines that cross one another, and a switching element connected to the gate line and the data line is further provided. The switching element is connected to the driving thin film transistor Tr, which is a driving element. In addition, a power line disposed spaced apart from and parallel to the gate line or data line, and a storage capacitor may be further included to constantly maintain a voltage of the gate electrode of the driving thin film transistor Tr, which is a driving element, during one frame.

Meanwhile, a passivation layer 350 having a drain contact hole 352 through which the drain electrode 342 of the driving thin film transistor Tr is exposed in such a way that it covers the driving thin film transistor Tr.

A first electrode 410 connected to the drain electrode 342 of the driving thin film transistor Tr though the drain contact hole 352 is formed on the passivation layer 350 for each pixel area. The first electrode 410 may be an anode or a cathode, and may consist of a conductive material having a relatively high work function. For example, the first electrode 410 may consist of a doped or undoped metal oxide such as ITO, IZO, ITZO, ICO, $SnO_2$, $In_2O_3$, Cd:ZnO, F:$SnO_2$, In: $SnO_2$, Ga: $SnO_2$ or AZO, or, other than the above-mentioned metal oxide, it may consist of a metal material including nickel (Ni), platinum (Pt), gold (Au), silver (Ag), iridium (Ir) or a CNT.

Meanwhile, when the QD light-emitting display device 300 of the present disclosure is of a top-emission type, a reflective electrode or a reflective layer may be further provided under the first electrode 410. For example, the reflective electrode or reflective layer may consist of an aluminum-palladium-copper (APC) alloy.

In addition, a bank layer 368 is formed on the passivation layer 350 to cover an edge of the first electrode 410. The bank layer 368 is configured to expose the center of the first electrode 410 corresponding to a pixel area.

An emissive layer 430 including the QDs 10, which are electroluminescent nanoparticles according to the present disclosure, is formed on the first electrode 410. The emissive layer 430 may consist only of an EML, or it may have multiple charge transfer layers to increase luminous efficiency. As an example, the first charge transfer layer 140 or 240 (see FIGS. 3 and 4) may be further formed between the first electrode 410 and the emissive layer 430, the second charge transfer layer 160 or 260 (see FIGS. 3 and 4) may be further formed between the emissive layer 430 and a second electrode 420.

The QD 10 in the emissive layer 430 may consist of a core 20, which is a luminous matter, and a shell 30 surrounding the core 20, and different types of ligands 42 and 44 bind to the surface of the shell 30. FIG. 5 illustrates that the X-type ligands 42 are positioned near the first electrode 410, and the L-type ligands 44 positioned near the second electrode 420. Alternatively, the X-type ligands 42 may be positioned near the second electrode 420, and the L-type ligands 44 may be positioned near the first electrode 410.

The second electrode 420 is formed on the emissive layer 430 formed on the substrate 310. The second electrode 420 may be disposed over the entire surface of a display area, consist of a conductive material having a relatively low work function, and may be a cathode or anode. For example, the second electrode 420 may be Ca, Ba, Ca/Al, LiF/Ca, LiF/Al, $BaF_2$/Al, CsF/Al, $CaCO_3$/Al, $BaF_2$/Ca/Al, Al, Mg, Au:Mg or Ag:Mg.

As described above, on the QD 10, which is a electroluminescent nanoparticle, the X-type ligands 42 having a negatively charged functional group and the L-type ligands 44 having a positively charged functional group are positioned such that each faces an electrode that is involved in generation, injection and transfer of a charge opposite that of the corresponding ligand. The holes and the electrons may be rapidly transferred, in equilibrium, to the emissive layer 430 due to the X-type ligands 42 and the L-type ligands 44, which have opposite charges to the holes and the electrons, respectively. Therefore, the QLED 400 and the QD light-emitting display device 300 including the same may have enhanced luminous efficiency, and the QLED 400 may be driven at a low voltage.

In addition, since a small quantity of organic components remain with the L-type ligand 44-binding QDs 10, the QDs 10 may be uniformly applied to form the emissive layer 430, and thus the emissive layer 430 may be controlled to have a uniform thickness. In addition, since the remaining organic components do not penetrate into the emissive layer 430 and the second electrode 420, the boundary between the emissive layer 430 and the second electrode 420 may be clearly distinguished, and the emissive layer 430 and the second electrode 420 may be formed with desired shapes or thicknesses.

Hereinafter, the present disclosure will be described through the following examples, but the present disclosure is not limited to the technical ideas described in the following examples.

SYNTHESIS EXAMPLE 1

Synthesis of Monolayer of QDs having X-Type Ligands and L-Type Ligands

1) Synthesis of ZnSe/ZnS Core/Shell QDs 0.073 g of Zn acetate, 0.237 g of oleic acid, and 0.032 g of Se were added to 26 mL of octadecene (ODE) as a solvent in a three-neck flask. The resulting mixture was heated in a vacuum state at 120° C. for 120 minutes to remove moisture, oxygen and impurities. After a change to an $N_2$ atmosphere, the resulting mixture was heated at 300° C. for 1 hour, thereby forming a ZnSe core. The core was cooled to a room temperature, and 7 mL of 0.4 M Zn oleate and 1 mL of 1 M tributyl phosphine sulfide (TBPS) were added to the flask, in which the core had been formed, to form a ZnS shell to which oleate, i.e., the X-type ligand, was bound. The resulting mixture was heated at 280° C. for 1 hour, thereby forming a ZnS shell. For work-up, a process of adding an excessive quantity of acetone and performing precipitation by centrifugation was repeated several times, and thus ZnSe/ZnS QDs to which the X-type ligands (i.e., oleate) were bound were ultimately synthesized.

2) Synthesis of Dual-Ligand-Binding QDs by TAEA Treatment

The QDs (ZnSe/ZnS) precipitated as described above were dispersed in hexane or toluene. The dispersion containing the QDs at a concentration of 10 mg/mL was applied to a substrate by spin coating (2000 rpm, 60 sec) and dried at 70° C. for 30 minutes. 1 to 2 mL of tris(2-aminoethyl) amine (TAEA) was dropped to the QD-coated surface, followed by spin coating (500 rpm, 30 sec). The resulting substrate was dried at 60 to 80° C. for 120 minutes to induce a ligand exchange at a part of the QD surface (a region not in contact with the substrate) by the diffusion according to the difference in the concentration of ligands and an interaction between Zn and an amino group. Work-up was performed once with resuspension of the resulting product in an organic solvent such as hexane or toluene.

SYNTHESIS EXAMPLE 2

Synthesis of Bilayer of QDs having X-Type Ligands and L-Type Ligands

The procedures described in Synthesis Example 1 were repeated, except that a concentration of applied ZnSe/ZnS core/shell QDs and a TAEA content were approximately doubled so as to arrange and apply the QDs as a bilayer on a substrate.

COMPARATIVE SYNTHESIS EXAMPLE

Synthesis of Monolayer of QDs Consisting only of X-Type Ligands

Unlike in Synthesis Example 1, QDs in which only X-type ligands (i.e., oleate) were bonded to the QD surface were synthesized without performing TAEA treatment.

Example 1

Measurement of Physical Properties of QDS

Figure 6:
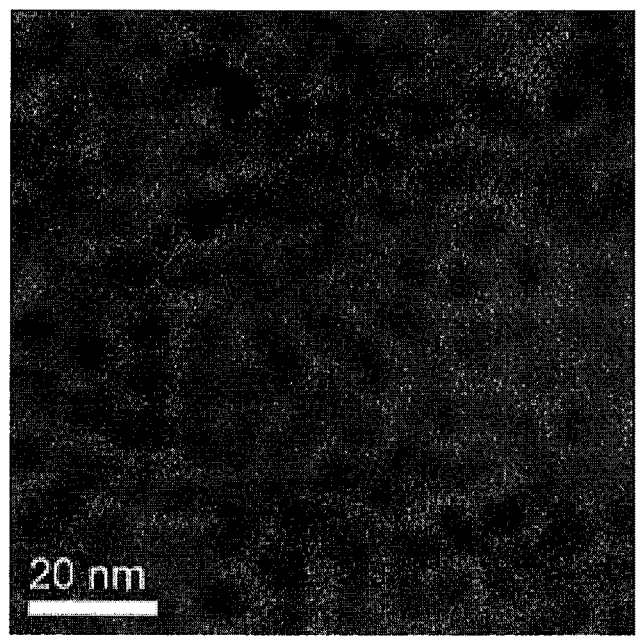
FIG. 6 is a transmission electrode microscope (TEM) image showing QDs according to an exemplary embodiment of the present disclosure, in which different types of ligands are bonded to the QD surface.
Figure 7:
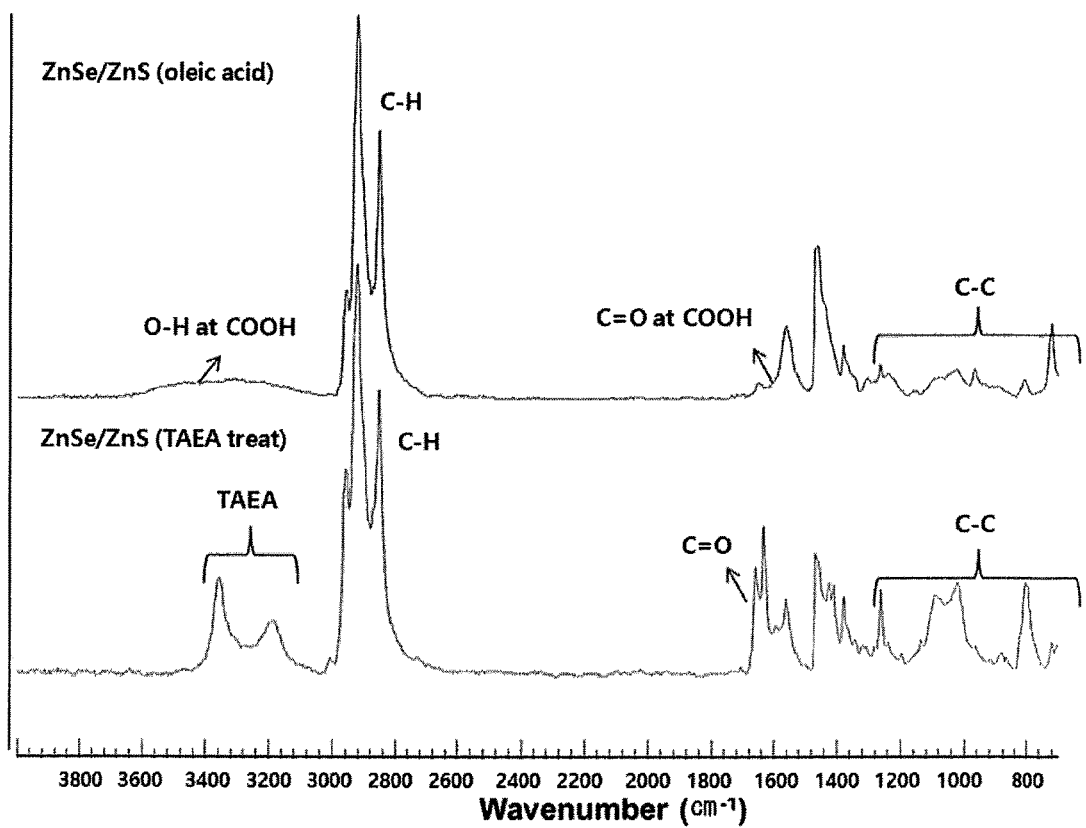
FIG. 7 is a graph illustrating a result of Fourier transform infrared spectroscopy (FT-IR) analysis for QDs synthesized according to an exemplary embodiment of the present disclosure, in which different types of ligands characteristics are bonded to the QD surface. A result of FT-IR analysis for QDs synthesized according to a comparative example, in which only X-type ligands are bonded to the QD surface, is also shown.

The physical properties of the QDs synthesized in Synthesis Example 1 were measured. To measure a particle size of the QD, 1 or 2 droplets of the QDs dispersed in hexane according to Synthesis Example 1 were dropped to a TEM grid, dried, and analyzed using TEM (Helios Nanolab 600i, FEI). FIG. 6 shows a TEM image of the QDs synthesized in Synthesis Example 1. An average particle size of the QD was 7.5 nm. In addition, the QDs dispersed in hexane according to Synthesis Example 1 were dissolved in sulfuric acid or hydrochloric acid, and subjected to inductively coupled plasma-mass spectroscopy (ICP-MS; ELAN DRC II, Perkin-Elmer). The analysis result shows that, in the synthesized QDs, a content of Zn atoms was 52.8 wt %, a content of Se atoms was 21.2 wt %, and a content of S atoms was 26.0%, suggesting that the QDs having a desired core/shell structure were synthesized. Moreover, FT-IR (FTS7000e, VARIAN) was performed by applying the dispersion containing the QDs in hexane (obtained Synthesis Example 1) to KBr or using powder-type QDs. The FT-IR result shows binding of TAEA ligands, which were not present on the QDs synthesized in the comparative example (see FIG. 7).

Figure 8A:
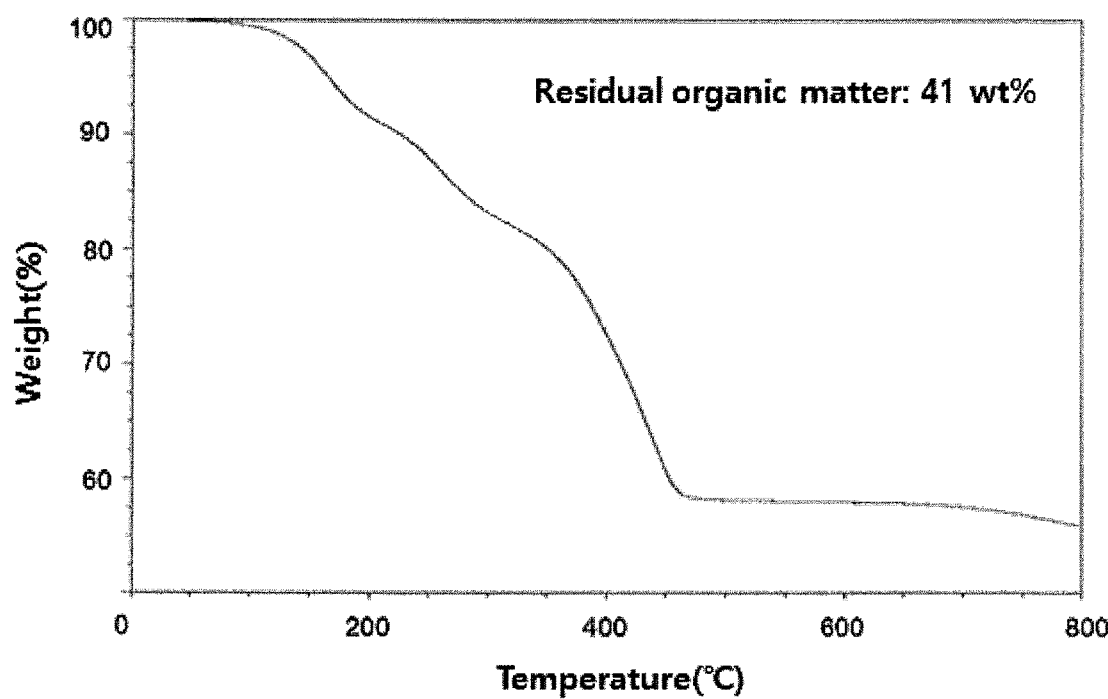
FIG. 8A is a graph illustrating a result of thermogravimetric analysis (TGA) for conventional QDs in which only X-type ligands are bonded to the QD surface.
Figure 8B:
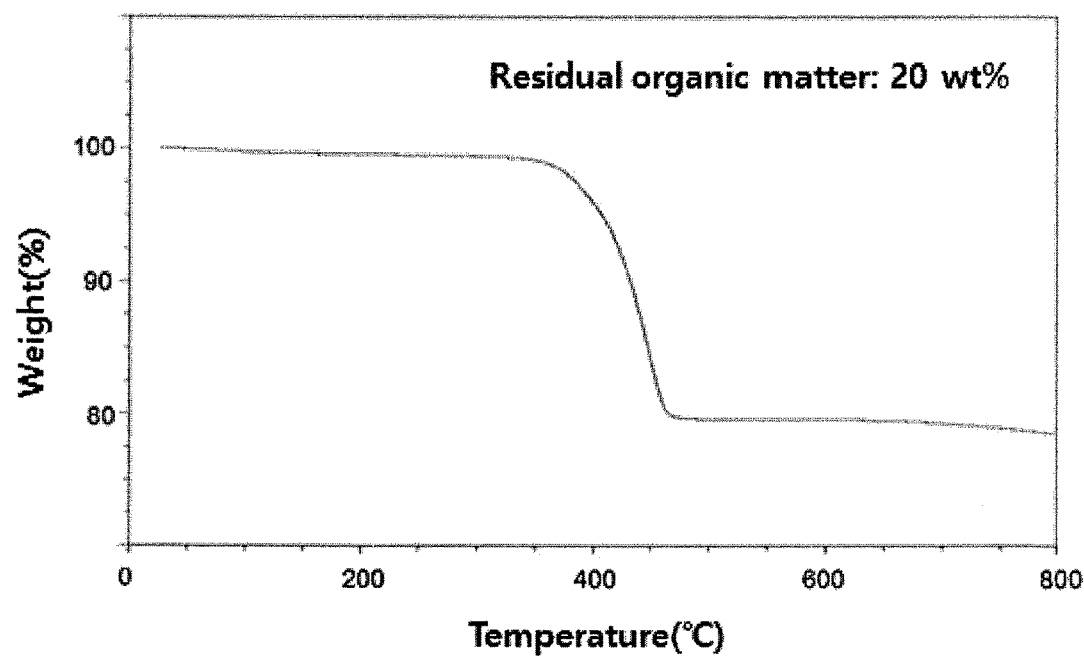
FIG. 8B is a graph illustrating a TGA result of QDs according to the present disclosure, in which X-type ligands and L-type ligands are bonded to two opposite parts in the QD surface.

Meanwhile, a powder prepared by drying the QDs synthesized in the comparative example was subjected to thermogravimetric analysis (TGA; Pyris1, Perkin-Elmer). As a result of TGA, it was confirmed that a considerable amount, i.e., 40 wt %, of the organic material remained (see FIG. 8A). On the other hand, according to the TGA for the QDs synthesized in Synthesis Example 1, a content of the remaining organic material was no more than 20 wt % (see FIG. 8B), indicating that the content of the remaining organic material was decreased to less than half in the case of the QDs in which the different types of ligands were bonded to the QD surface.

Subsequently, to confirm if different types of ligands had been bonded to different regions on the QD surface, TOF-SIMS analysis was performed. One hour after a silicon wafer was treated with UV-ozone, a specimen was prepared by applying the dispersion containing the QDs in hexane obtained in Synthesis Example 1 to the wafer by spin coating (2,000 rpm, 60 sec) and was analyzed, starting from the most distant part from the wafer and ending at the closest part to the wafer, at predetermined time intervals. FIG. 9 shows a result of TOF-SIMS analysis for the QDs synthesized in Synthesis Example 1. As shown in FIG. 9, from the QD surface most distant from the wafer and not covered by the wafer, carbon-nitrogen bonds included in the TAEA ligands, i.e., the L-type ligands, were mainly detected, and almost no —O bonds included in the X-type ligands were detected. However, as the distance to the wafer decreased, the content of the L-type ligands decreased and the content of the X-type ligands increased, and it was confirmed that the X-type ligands, which had been previously bonded, were mainly bonded to the QD surface covered by the wafer.

In addition, as a result of measuring photoluminescence (PL) intensity and quantum yield (QY) for the QDs synthesized in Synthesis Example 1, it was confirmed that the PL intensity and the quantum yield were similar to those of the QDs synthesized in the comparative synthesis example (the result was not shown), suggesting that there was no difference in optical characteristics.

Example 2

Manufacture of QLED

An LED employing a monolayer of QDs synthesized according to Synthesis Example 1 was manufactured. ITO (anode, 50 nm) was treated with UV-ozone for 1 hour, and then emissive layers and a cathode were stacked in the following order: a HIL (PEDOT:PSS, spin-coating (2000 rpm) and the drying at 120° C. for 30 minutes; 25 nm), a HTL (HTL, TFB, spin-coating (2000 rpm) and then drying at 120° C. for 30 minutes; 24 nm), an EML (EML, QDs of Synthesis Example 1, spin-coating (2000 rpm) and then drying at 70° C. for 60 minutes; 18 nm), an ETL (TPBi, deposition ($3\times10^{-6}$ Torr, 0.1 Å/s); 52 nm), and a cathode (Al, $3\times10^{-6}$ Torr, 4 to 5 Å/s); 80 nm).

Example 3

Manufacture of QLED

A QLED was manufactured by repeating the procedures of Example 2, except that a bilayer of QDs according to Synthesis Example 2 was used for an EML.

COMPARATIVE EXAMPLE

Manufacture of QLED

A QLED was manufactured by repeating the procedures of Example 2, except that the QDs according to the comparative synthesis example, in which QDs, bounding only the X-type ligands to its surface, were used for an EML.

Example 4

Evaluation of Physical Properties of QLED

1) Evaluation of Luminescence Characteristics

A driving voltage (V), a driving current (A), a current density (mA/cm$^2$), current efficiency (Cd/A), power efficiency (lm/W_, external quantum efficiency (EQE) and luminance (Cd/m$^2$) of each of the LEDs manufactured in Example 1 and Comparative Example were measured. A measurement result is shown in Table 1.

TABLE 1

| Luminance characteristics of QLEDs | | | | | | |
|---|---|---|---|---|---|---|
| V | A | mA/cm$^2$ | Cd/A | lm/W | EQE (%) | Cd/m$^2$ |
| Example 1 | 5.525 | 0.0009 | 10 | 1.682 | 0.956 | 2.278 | 168.2 |
| Comparative Example | 3.986 | 0.009 | 10 | 0.1012 | 0.079 | 0.146 | 10.12 |

As shown in Table 1, when the QDs in which the X-type ligands and the L-type ligands were bonded to specific regions of the QD surface were applied to an EML, compared with when the QDs in which only X-type ligands were bonded to the QD surface were applied to the EML, the driving voltage decreased by 38.6%, and the current decreased 10-fold. In addition, at the same current density, the current efficiency increased 16.6-fold, the power efficiency increased 12.1-fold, the external quantum yield increased 15.6-fold, and the luminance increased 16.6-fold. Therefore, it was confirmed that, when the QDs according to the present disclosure, in which different types of ligands were bonded to specific regions of the QD surface, were applied to the EML, the QLED which can be driven at a low voltage and has highly enhanced luminous efficiency may be realized and applied to a QD light-emitting device.

2) Evaluation of Morphology of Layers Constituting QLED

Figure 10A:
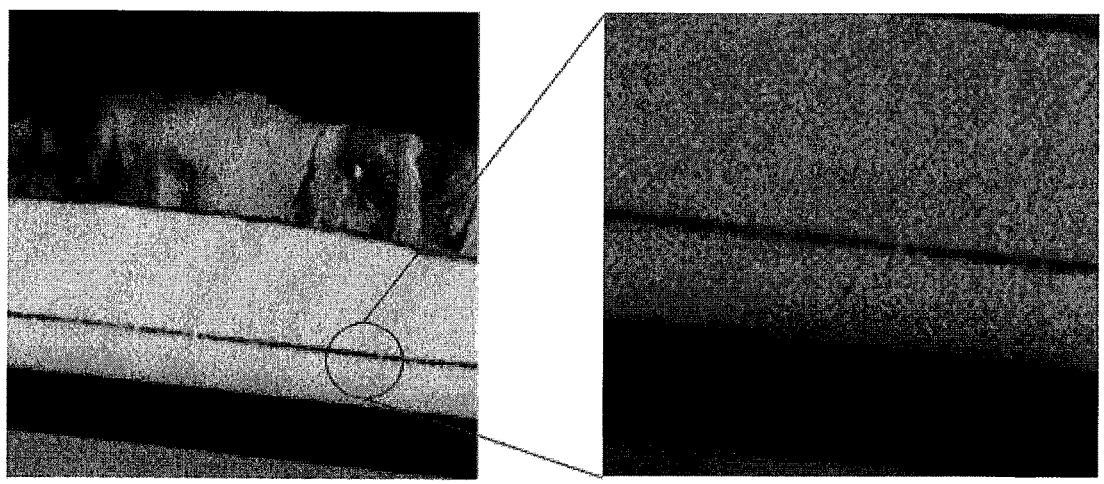
FIGS. 10A and 10B are TEM images schematically illustrating the cross-sectional structures of EMLs, which are formed by applying a monolayer (FIG. 10A) and a bilayer (FIG. 10B) of QDs synthesized according to an exemplary embodiment of the present disclosure, in which different types of ligands are bonded to the QD surface.
Figure 10B:
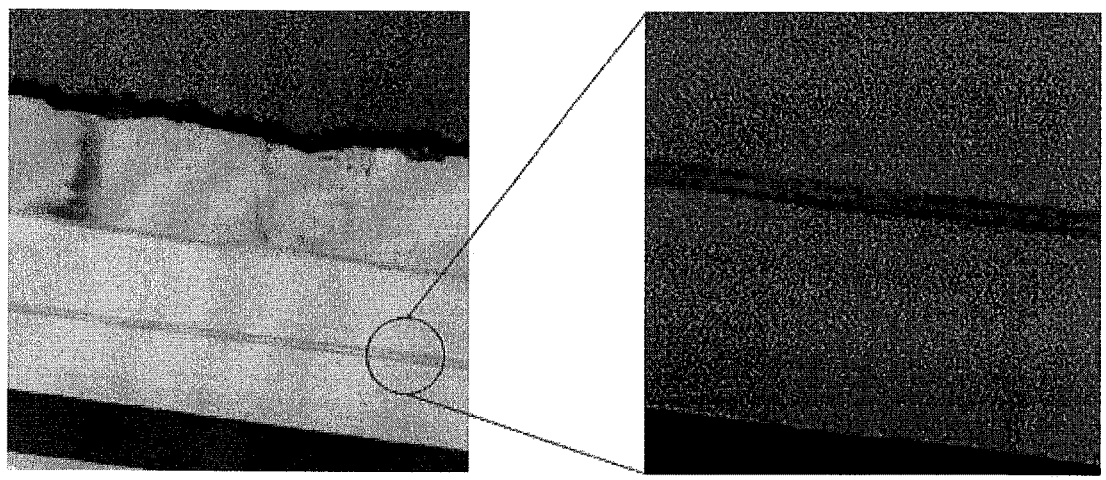

The morphology of layers in each of the LEDs manufactured in Examples 2 and 3 and Comparative Example was evaluated using TEM. FIGS. 10A and 10B are electron microscope images schematically illustrating the cross-sectional structures of EMLs consisting of a monolayer (FIG. 10A) and a bilayer (FIG. 10B) of QDs synthesized according to an exemplary embodiment of the present disclosure, in which ligands having different characteristics are bonded to the QD surface. It is confirmed that, since the two types of ligands having different charge characteristics were bonded to specific regions of the QD surface, it was confirmed that the QDs may be applied as a monolayer or bilayer, thereby easily adjusting or controlling a thickness of the EML.

Figure 11A:
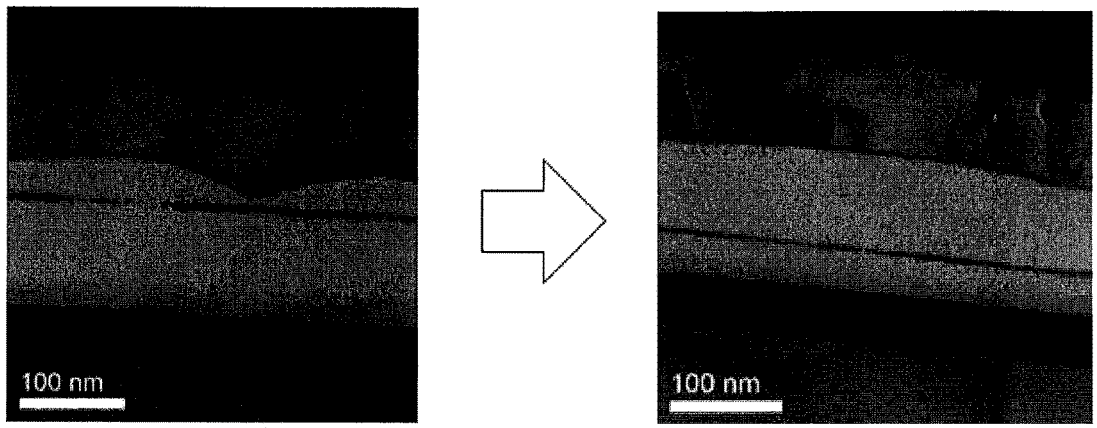
FIGS. 11A and 11B are TEM images schematically illustrating the cross-sectional structure of an LED having an EML formed by applying QDs synthesized according to an exemplary embodiment of the present disclosure, in which different types of ligands are bonded to the QD surface.
Figure 11B:
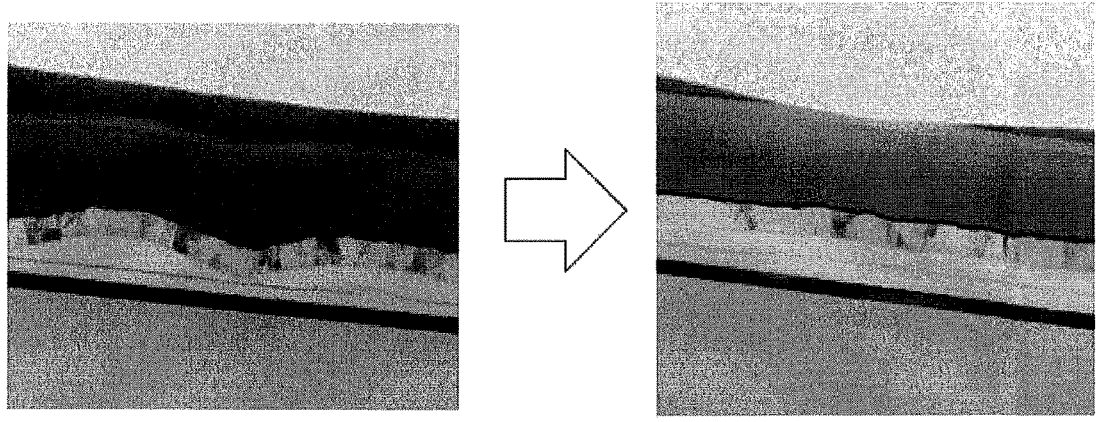

Meanwhile, FIGS. 11A and 11B are electron microscope images schematically showing the cross-sectional structure of an LED having an EML by applying QDs synthesized according to an exemplary embodiment of the present disclosure, in which ligands having different characteristics are bonded to the QD surface. As shown in the image on the left side of each of FIGS. 11A and 11B, when the EML was formed using the QDs in which only X-type ligands were bonded to the QD surface, a thickness of the EML was not uniform, and an ETL and a second electrode were not stacked with desired shapes. In contrast, as shown in the image on the right side of each of FIGS. 11A and 11B, when the QDs according to the present disclosure, which has both the X-type ligands and the L-type ligands bonded to specific regions of the QD surface, were used in the EML, a thickness of the EML can be uniformly controlled, and the ETL and the second electrode can be easily formed with desired shapes.

According to the present disclosure, QDs in which X-type ligands are bonded to a first region of the surface of a QD particle, and L-type ligands are bonded to a second region of the QD surface, which is an opposite part of the first region, are applied in an EML.

As QDs in which two different types of ligands bind to specific regions of the QD surface are used, balanced transfer of charges to the EML can be achieved, and thereby a QLED and a light-emitting device that can be driven at a lower driving voltage and have enhanced luminous efficiency can be manufactured and realized.

In addition, organic components remaining on the QD surface can be reduced by a ligand exchange reaction. Therefore, an EML to which the QDs according to the present disclosure are introduced can be effectively controlled to a desired thickness, and the EML, and a charge transfer layer and an electrode formed adjacent thereto can be easily formed.

Therefore, with the use of the QDs in which two different types of ligands are introduced to the QD surface, a QLED which has enhanced luminous efficiency, low driving voltage, an EML easily controlled to have a desired thickness, and a charge transfer layer and an electrode with suitable shapes, and a QD light-emitting device using the same may be manufactured.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the disclosure. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A quantum dot comprising:
   a semiconductor nanocrystal or metal oxide core;
   a shell substantially or fully covering the core, wherein the shell has an outer surface;
   an X-type ligand comprising a functional group selected from the group consisting of a carboxylate group, a phosphate group, and a thiolate group bound to a first region of the outer surface; and
   an L-type ligand comprising a functional group selected from the group consisting of an amino group, a thiol group, a phosphine group, and a phosphine oxide group bound to a second region of the outer surface.

2. The quantum dot of claim 1, wherein the X-type ligand further comprises a $C_5$-$C_{30}$ saturated or unsaturated hydrocarbon chain.

3. The quantum dot of claim 1, wherein the X-type ligand has one of the following structures:

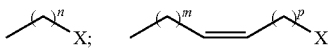

wherein:
   n is an integer ranging from 6 to 16;
   m is an integer ranging from 4 to 9;
   p is an integer ranging from 4 to 9; and
   X is a carboxylate group, a phosphate group, or a thiolate group.

4. The quantum dot of claim 3, wherein the X-type ligand is selected from the group consisting of octanoic acid, decanoic acid, dodecanoic acid, myristic acid, palmitic acid, hexadecanoic acid, stearic acid, oleic acid, and combinations thereof.

5. The quantum dot of claim 1, wherein the L-type ligand is selected from the group consisting of $C_1$ to $C_{10}$ linear or branched alkyl amines, $C_4$ to $C_8$ alicyclic amines, $C_5$ to $C_{20}$ aromatic amines, $C_1$ to $C_{10}$ linear or branched alkyl phosphines, $C_1$ to $C_{10}$ linear or branched alkyl phosphine oxides and a combination thereof.

6. The quantum dot of claim 1, wherein the L-type ligand is tris(2-aminoethyl)amine, tris(2-aminomethyl)amine, N-butyl-N-ethylethane-1,2-diamine, ethylene diamine, pentaethylenehexamine, cyclohexane-1,2-diamine, cyclohexene-1,2-diamine, or 2,3-diaminopyridine.

7. The quantum dot of claim 1, wherein the X-type ligand is bound to the first region of the outer surface through a negatively charged functional group.

8. The quantum dot of claim 1, wherein the L-type ligand is bound to the second region of the outer surface through an unshared electron pair.

9. The quantum dot of claim 1, wherein the outer surface is substantially spherical and the first region is a first hemisphere and the second region is a second hemisphere.

10. A light emitting diode comprising a plurality of quantum dots according to claim 1.

11. The light emitting diode of claim 10 comprising:
    a first electrode and a second electrode;
    an emitting material layer;
    an electron transfer layer; and
    a hole transfer layer
    wherein
    the emitting material layer is interposed between the electron transfer layer and the hole transfer layer and the emitting material layer comprises the quantum dots.

12. The light emitting diode of claim 11, wherein a plurality of the first regions of the outer surfaces of the quantum dots are substantially proximal to the hole transfer layer and substantially distal to the electron transfer layer.

13. The light emitting diode of claim 11, wherein a plurality of the second regions of the outer surfaces of the quantum dots are substantially proximal to the electron transfer layer and distal to the hole transfer layer.

14. A light emitting device comprising a quantum dot of claim 1.

15. The light emitting device of claim 14 comprising:
    a substrate;
    a light emitting diode comprising the quantum dot of claim 1 on the substrate; and
    a driving element disposed between the substrate and the light emitting diode and connected to the light emitting diode.

16. A light emitting device comprising a light-emitting diode of claim 10.

17. The light emitting device of claim 16 comprising:
    a substrate;
    a light emitting diode comprising the quantum dot of claim 1 on the substrate; and
    a driving element disposed between the substrate and the light emitting diode and connected to the light emitting diode.

* * * * *